United States Patent
Gold et al.

(10) Patent No.: US 11,521,717 B2
(45) Date of Patent: Dec. 6, 2022

(54) SYSTEM AND METHOD FOR GENERATING AND UPDATING A USER INTERFACE TO EVALUATE AN ELECTRONIC MEDICAL RECORD

(71) Applicant: Intelligent Medical Objects, Inc., Rosemont, IL (US)

(72) Inventors: Jonathan Gold, Louisville, CO (US); Regis Charlot, Lake Bluff, IL (US); Jose A. Maldonado, Chicago, IL (US); James Thompson, St. Charles, IL (US); Fred Masarie, Husum, WA (US); Ivana Naeymi-Rad, Libertyville, IL (US); Alex Burck, Mount Prospect, IL (US); Yun Wu, Arlington Heights, IL (US); Emil Setiawan, Oak Park, IL (US); Emma Lee Foley, Chicago, IL (US); Frank Naeymi-Rad, Libertyville, IL (US); Steven Rube, Lake Forest, IL (US)

(73) Assignee: INTELLIGENT MEDICAL OBJECTS, INC., Rosemont, IL (US)

( * ) Notice: Subject to any disclaimer, the term of this patent is extended or adjusted under 35 U.S.C. 154(b) by 454 days.

(21) Appl. No.: 16/803,999

(22) Filed: Feb. 27, 2020

(65) Prior Publication Data
US 2020/0202988 A1    Jun. 25, 2020

Related U.S. Application Data

(63) Continuation-in-part of application No. 15/458,711, filed on Mar. 14, 2017, now abandoned, which is a
(Continued)

(51) Int. Cl.
*G16H 10/60*    (2018.01)

(52) U.S. Cl.
CPC .................................. *G16H 10/60* (2018.01)

(58) Field of Classification Search
CPC .............................. G16H 10/60; G06F 19/322
See application file for complete search history.

(56) References Cited

U.S. PATENT DOCUMENTS

| | | |
|---|---|---|
| 5,799,268 A | 8/1998 | Boguraev |
| 5,930,788 A | 7/1999 | Wical |

(Continued)

OTHER PUBLICATIONS

"Semantic Web: Asking the Right Questions," Duch et al.. Seventh International Conference on Information and Management Sciences, Urumchi, China, Aug. 12-19, 2008 entire document www.fizyka.umk.pl/ftp/pub/papers/kmk/08-SemWeb.pdf.
(Continued)

*Primary Examiner* — Devin C Hein
(74) *Attorney, Agent, or Firm* — Quarles & Brady LLP

(57) ABSTRACT

A method for generating a user interface for analyzing a patient-specific electronic medical or health record that includes a problem list includes the steps of grouping related potential problems into problem list categories, grouping a subset of the problems into clusters within the categories, mapping, using a computer, entries in the problem list with a respective description in an interface terminology, associating one or more of other medical data, e.g., medication, lab results, procedures, imaging results, past medical history or surgeries, notes, vital signs, or allergy data in the record withdf at least one problem, receiving a request corresponding to a problem or problem list category or to other medical data, identifying non-problem data in the record grouped in a cluster with the requested data, and modifying a user interface to display the identified data separate from other similar medical data included in the electronic medical or health record.

4 Claims, 21 Drawing Sheets

Related U.S. Application Data continuation of application No. 14/530,727, filed on Nov. 1, 2014.

(60) Provisional application No. 61/943,109, filed on Feb. 21, 2014.

(56) References Cited

U.S. PATENT DOCUMENTS

| | | | |
|---|---|---|---|
| 6,055,540 | A | 4/2000 | Snow |
| 6,101,515 | A | 8/2000 | Wical |
| 6,904,432 | B2 | 6/2005 | Charlot |
| 7,167,858 | B2 | 1/2007 | Naeymi-Rad |
| 7,496,593 | B2 | 2/2009 | Gardner |
| 7,536,387 | B2 | 5/2009 | Charlot |
| 7,693,917 | B2 | 4/2010 | Charlot |
| 7,711,671 | B2 | 5/2010 | Meyers |
| 7,870,117 | B1 | 1/2011 | Rennison |
| 8,346,804 | B2 | 1/2013 | Phillips |
| 2002/0128861 | A1 | 9/2002 | Lau |
| 2003/0179228 | A1 | 9/2003 | Schreiber |
| 2005/0240572 | A1 | 10/2005 | Sung |
| 2006/0069677 | A1 | 3/2006 | Tanigawa |
| 2007/0179776 | A1 | 8/2007 | Segond |
| 2008/0065452 | A1 | 3/2008 | Naeymi-Rad |
| 2008/0306926 | A1 | 12/2008 | Friedlander |
| 2009/0083231 | A1 | 3/2009 | Eberholst |
| 2009/0150289 | A1 | 6/2009 | Joe |
| 2009/0254572 | A1 | 10/2009 | Redlich |
| 2010/0169299 | A1 | 7/2010 | Pollara |
| 2010/0262659 | A1 | 10/2010 | Christiansen |
| 2011/0066425 | A1 | 3/2011 | Hudgins |
| 2011/0138050 | A1 | 6/2011 | Dawson |
| 2011/0184960 | A1 | 7/2011 | Delpha |
| 2012/0011124 | A1 | 1/2012 | Bellegarda |
| 2012/0179696 | A1 | 7/2012 | Charlot |
| 2012/0239671 | A1 | 9/2012 | Chaudri |
| 2013/0262142 | A1 | 10/2013 | Sethumadhavan |
| 2013/0282713 | A1 | 10/2013 | Lawrence |
| 2015/0039343 | A1 | 2/2015 | Cline |
| 2016/0019361 | A1 | 1/2016 | Zasowski |

OTHER PUBLICATIONS

Virginia Tech SNOMED Core Structures 2nd AAHA Software Vendors Summit, Apr. 21, 2009.
"Social tagging overview (SharePoint Server 2010)" May 12, 2010 entire document http://technet.microsoft.com/en-us/library/ff608137.aspx.
Bronnert et al., Problem-Centered Care Delivery, Journal of AHIMA 83, No. 7 (Jul. 2012): 30-35.

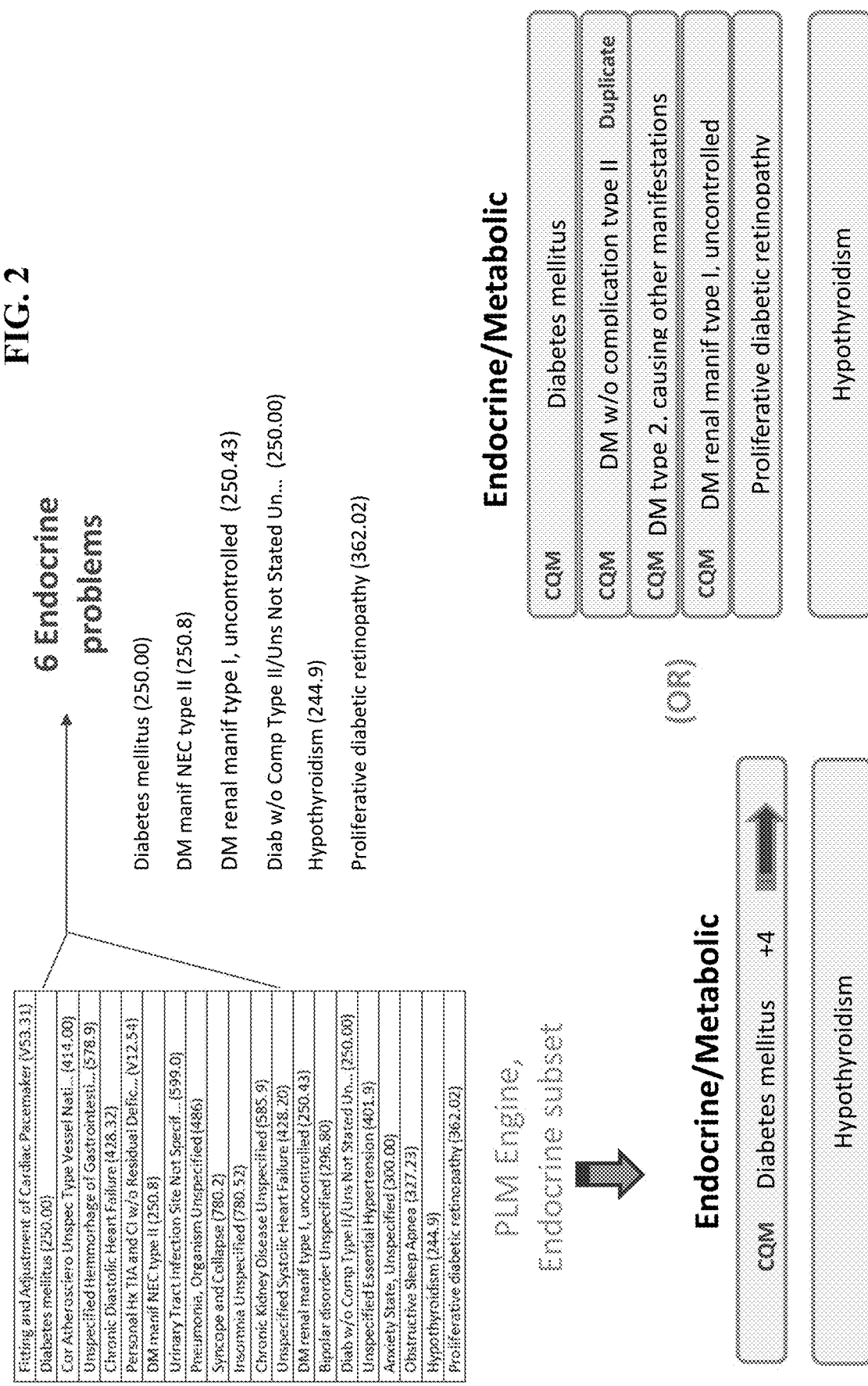

FIG. 3

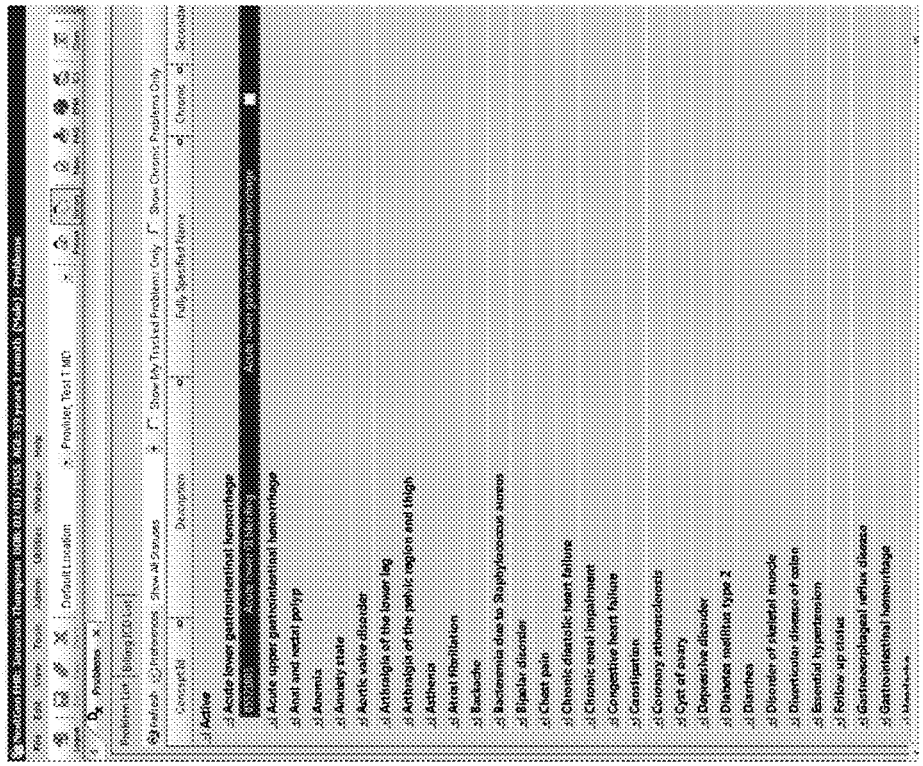

| | |
|---|---|
| PROBLEM 1 | PROBLEM 21 |
| PROBLEM 2 | PROBLEM 22 |
| PROBLEM 3 | PROBLEM 23 |
| PROBLEM 4 | PROBLEM 24 |
| PROBLEM 5 | PROBLEM 25 |
| PROBLEM 6 | PROBLEM 26 |
| PROBLEM 7 | PROBLEM 27 |
| PROBLEM 8 | PROBLEM 28 |
| PROBLEM 9 | PROBLEM 29 |
| PROBLEM 10 | PROBLEM 30 |
| PROBLEM 11 | PROBLEM 31 |
| PROBLEM 12 | PROBLEM 32 |
| PROBLEM 13 | PROBLEM 33 |
| PROBLEM 14 | PROBLEM 34 |
| PROBLEM 15 | PROBLEM 35 |
| PROBLEM 16 | PROBLEM 36 |
| PROBLEM 17 | PROBLEM 37 |
| PROBLEM 18 | PROBLEM 38 |
| PROBLEM 19 | PROBLEM 39 |
| PROBLEM 20 | PROBLEM 40 |

- Septic arthritis of knee, right
- Lymphedema of lower extremity
- Chronic kidney disease, stage III (moderate)
- Hyperparathyroidism due to renal insufficiency
- Hypertensive disorder
- History of kidney transplant
- Infected traumatic ulcer of lower extremity
- Anemia in chronic kidney disease
- Pseudomonas aeruginosa infection

Reconciled Problem List

| Top of Display | | Renal |
|---|---|---|
| Personal History of Methicillin Resistant Staph... | | Lower urinary tract infectious disease |
| Sensitive | | Renal Impairment |
| Bipolar Disorder Unspecified | | Respiratory |
| Cardiovascular | | Pneumonia, Organism Unspecified |
| Congestive Heart Failure | | Cough, persistent |
| Unspecified COM...more | | Sinusitis |
| Unspecified Essential Hypertension | | Signs and Symptoms |
| Atrial Fibrillation | | Syncope and Collapse |
| Mitral Valve Insuff&Aortic Valve Insuff | | Other |
| Endocrine | | Annual Physical Exam |
| Type 2 diabetes mellitus without complication | | |
| Hyperlipidemia | | |
| Hypothyroidism | | |
| Gastrointestinal | | |
| Esophageal Reflux | | |
| Ulcer of Esophagus Without Bleeding | | |
| Constipation | | |
| Irritable Bowel Syndrome | | |
| Hematology Oncology | | |
| Anemia | | |
| Musculoskeletal | | |
| Dorsalgia | | |
| Neuro | | |
| Epilepsy | | |
| Personal history of TIA | | |

Problem List

| Top Level Focus | | Musculoskeletal |
|---|---|---|
| Personal History of Methicillin... | | Dorsalgia |
| Sensitive | | Neuro |
| Bipolar Disorder Unspecified | | Epilepsy |
| | | Personal Hx TIA |
| Cardiovascular | | Renal |
| Congestive Heart Failure COM...more | | Urinary Tract Infection |
| Unspecified Essential Hypertension | | Chronic Kidney Disease Unspecified |
| Mitral Valve Insuff/Aortic Valve Insuff | | Respiratory |
| Atrial Fibrillation | | Pneumonia, Organism Unspecified |
| Endocrine | | Cough, persistent |
| Type 2 diabetes mellitus w/o complication | | Signs and Symptoms |
| Gastrointestinal | | Syncope and Collapse |
| Esophageal Reflux | | Other |
| Ulcer of Esophagus Without Bleeding | | Annual Physical Exam |
| Constipation | | |
| Irritable Bowel Syndrome | | |
| Hematology Oncology | | |
| Anemia | | |

CCDA LIST

| |
|---|
| Lower urinary tract infectious disease 4009004 |
| Gastroesophageal reflux disease 235595009 |
| Congestive Heart Failure Unspecified 54158009 |
| Constipation 14760008 |
| Depressive disorder 35489007 |
| Seizure Disorder 128613002 |
| Hypothyroidism 40930008 |
| Atrial Fibrillation 49436004 |
| Sinusitis 36971009 |
| Hypertensive disorder 38341003 |
| Acute upper respiratory infection 54398005 |
| Methicillin resistant staph aureus carrier 432415000 |
| Renal impairment 236423003 |

FIG. 4

EHR Problem List

Top of Display

Personal history of methicillin resis staph infection

Sensitive
Bipolar disorder, unspecified

Cardiovascular
Congestive heart failure, unspecified    CCIII   ...more
Unspecified essential hypertension
Mitral valve insufficiency and aortic valve insufficiency
Atrial fibrillation

Endocrine
Type 2 diabetes mellitus without complication
Hyperlipidemia

Gastrointestinal
Esophageal Reflux
Ulcer of esophagus without bleeding
Constipation
Irritable bowel syndrome

Hematology/Oncology
Anemia

Musculoskeletal
Dorsalgia

Neuro
Epilepsy
Personal history of TIA

Renal
Urinary tract infection
Chronic kidney disease unspecified

Respiratory
Pneumonia, organism unspecified
ACE-inhibitor cough

Signs and Symptoms
Syncope and collapse

Other
Physical exam, annual

---

CCDA List for Import

Lower urinary tract infectious disease  4009004
Gastroesophageal reflux disease  235595009
Congestive heart failure  42343007
Constipation  14760008
Depressive disorder  35489007
Seizure disorder  128613002
Hypothyroidism  40930008
Atrial Fibrillation  49436004
Sinusitis  36971009
Essential hypertension  59621000
Acute upper respiratory infection  54398305
Methicillin resistant staph aureus carrier  432415000
Renal impairment  236423003

FIG. 5

Reconciled Problem List

Top of Display

Personal History of Methicillin Resistant Staph....

*Sensitive*

Bipolar Disorder Unspecified

Cardiovascular

Congestive Heart Failure Unspecified COM ...more
Unspecified Essential Hypertension
Atrial Fibrillation
Mitral Valve Insuff&Aortic Valve Insuff

Endocrine

Type 2 diabetes mellitus without complication
Hyperlipidemia
Hypothyroidism

Gastrointestinal

Esophageal Reflux
Ulcer of Esophagus Without Bleeding
Constipation
Irritable Bowel Syndrome

HematologyOncology

Anemia

Musculoskeletal

Dorsalgia

Neuro

Epilepsy
Personal history of TIA

Renal

Lower urinary tract infectious disease
Renal Impairment

Respiratory

Pneumonia, Organism Unspecified
Cough, persistent
Sinusitis

Signs and Symptoms

Syncope and Collapse

Other

Annual Physical Exam

Problems

| | Risk | Onset Date | Resolved Date |
|---|---|---|---|
| Cardiac and Vasculature | | | |
| Congestive heart failure with left ventricular diastolic dysfunction, NYHA class 1 | ⬤ | 11/20/17 | |
| Status post myocardial infarction | ⬤ | 04/30/07 | |
| Hyperlipidemia with low HDL | | | |
| Hypertension | | 02/20/05 | |
| Endocrine and Metabolic | | | |
| Diabetes mellitus, type 2, insulin dependent | | | |
| Eye | | | |
| Diabetic retinopathy without macular edema | ⬤ | 11/20/17 | |
| Genitourinary and Reproductive | | | |
| End stage renal disease | ⬤ | 06/20/18 | |
| Chronic kidney disease, stage 4 (severe) | ⬤ | 11/20/17 | |
| CKD (Chronic kidney disease), stage III | | 04/30/07 | |
| Stage 1 chronic kidney disease | | 02/20/05 | |
| | | 10/23/02 | |
| Neuro | | | |
| Peripheral neuropathy | | 11/20/17 | |

Medications

| Drug | Start Date | End Date | Dosage | Care Provider |
|---|---|---|---|---|
| Lisinopril, PO | 9/1/2016 | | 40mg x 1 | Alice Simple |
| Atorvastatin, PO | 4/15/2006 | | 10mg x 1 | Alice Simple |
| Hydralazine HCl, PO | 6/6/2005 | | 50mg x 4 | Patricia Primary |
| Isosorbide Mononitrate, SL | 12/19/1997 | | 2.5mgPRN | George Happy |
| Insulin Glargine, SC | 09/26/2015 | | 24oU/mL x1 | Alice Simple |
| Insulin Lispro, SC | 05/04/2015 | | 15oU/mL x4 | Alice Simple |
| Timolol, Ophthalmic Drops 0.5%, OU | 04/12/2016 | | 1 drop x2 | Alice Simple |

Lab Results

| Test Performed | Test Result | Reference Range | Flags | Date |
|---|---|---|---|---|
| Glucose | 270 | 70-100mg/dL | ++ | 5/7/2019 |
| Hemoglobin A1c | 7.9 | 5.7-6.4% | + | 5/7/2019 |
| Cholesterol, Tot | 281 | 140-220mg/dL | ++ | 01/24/2017 |
| HDL | 45 | 40-65mg/dL | = | 01/24/2017 |
| LDL | 160 | 80-100mg/dL | + | 01/24/2017 |
| LDL:HDL Ratio | 3.55 | 1.00-3.64 | = | 01/24/2017 |
| VLDL | 65 | 8-25mg/dL | ++ | 01/24/2017 |
| Triglycerides | 210 | 40-150mg/dL | + | 01/24/2017 |

Procedures

| Procedure | Date | Location | Care Provider |
|---|---|---|---|
| EKG | 03/09/2019 | Healthy Heart Cl. | Virginia Stevens |
| Laser photocoagulation, both eyes | 07/07/2018 | The Eye Clinic | Rachel Kline |
| Hemodialysis | 06/04/2009 | Dialysis 'R Us | Ted Lincoln |
| Arteriovenous fistula creation | 07/18/2009 | Dialysis 'R Us | Sandra Knight |
| Peritoneal dialysis | 11/27/2008 | Dialysis 'R Us | |
| Radionuclide ventriculography | 7/12/2007 | Healthy Heart Cl. | Earl Grave |
| Stress test | 6/15/2007 | Healthy Heart Cl. | Robert Peck |
| Placement of stent into circumflex... | 04/30/2007 | Northbrook IM. | Brian Tinkerer |
| EKG | 04/30/2007 | Northbrook IM. | |

SYSTEM AND METHOD FOR GENERATING AND UPDATING A USER INTERFACE TO EVALUATE AN ELECTRONIC MEDICAL RECORD

This application is a continuation-in-part of U.S. application Ser. No. 15/458,711, filed Mar. 14, 2017, which is a continuation of U.S. application Ser. No. 14/530,727, filed Nov. 1, 2014, which claims priority to U.S. provisional application 61/943,109, filed Feb. 21, 2014, each of which is incorporated herein by reference in its entirety.

BACKGROUND OF THE INVENTION

Patient electronic medical records (EMRs) are used to store a patient's medical history in one location. EMRs permit more complete recordkeeping, which may lead to improved patient care, as healthcare professionals may be able to quickly and thoroughly review the patient's previous and current medical conditions in one location. EMRs also may facilitate portability of healthcare records.

As computer use has become more prevalent, electronic health records or electronic medical records (EHRs or EMRs) have become the industry standard for documenting patient care. Industry initiatives and government legislation have facilitated EHR implementation and use. Most notable among them is the Health Information Technology for Economic and Clinical Health Act (HIT ECH), which gives incentives to providers toward implementation and demonstration of meaningful EHR use.

An aspect of reliable and accurate information is ensuring that providers have the ability to capture their clinical intentions regarding patient care through terminologies. Healthcare terminology has long been called "the language of medicine," but, in the electronic age, this language has to be readable by both humans and computers. Various terminologies are used in defining associated terms.

Terminology

Terminology is a set of descriptions used to represent concepts specific to a particular discipline. It also is the foundation of EHR data. For example, the terms "heart attack" and "MI" describe the same concept of myocardial infarction. The concept in turn may be associated with codes that are used for a variety of purposes.

Different healthcare terminologies may have their own unique features and purposes. For example, one set of terminologies, RxNorm, encodes medications, while another set of terminologies, e.g., Logical Observation Identifiers Names and Codes (referred to under the trademark "LOINC"), is used for laboratory results.

Terms related to terminology include: Administrative code sets; Clinical code sets; and Reference terminologies.

Administrative code sets may be designed to support administrative functions of healthcare, such as reimbursement and other secondary data aggregation. Common examples are the International Classification of Disease (ICD) and the Current Procedural Terminology, which is referred to via the trademark CPT. Each system may be different, e.g., ICD's purpose is to aggregate, group, and classify conditions, whereas CPT is used for reporting medical services and procedures.

Clinical code sets have been developed to encode specific clinical entities involved in clinical work flow, such as LOINC and RxNorm. Clinical code sets have been developed to allow for meaningful electronic exchange and aggregation of clinical data for better patient care. For example, sending a laboratory test result using LOINC facilitates the receiving facility's ability to understand the result sent and make appropriate treatment choices based upon the laboratory result.

A reference terminology may be considered a "concept-based, controlled medical terminology." The Systematized Nomenclature of Medicine Clinical Terms (referred to under the trademark "SNOMED CT") is an example of this kind of terminology. It maintains a common reference point in the healthcare industry. Reference terminologies also identify relationships between their concepts. Relationships can be hierarchically defined, such as a parent/child relationship. The reference terminology contains concept A and concept B, with a defined relationship of B as a child of A. SNOMED CT includes concepts such as heart disease and heart valve disorder, and their defined relationship identifies heart valve disorder as a child of heart disease.

Reference terminology may allow healthcare systems to get value from clinical data coded at the point of care. In general, reference terms may be useful for decision support and aggregate reporting and may be more general than the highly detailed descriptions of actual patient conditions. For example, one patient may have severe calcific aortic stenosis and another might have mild aortic insufficiency; however, a healthcare enterprise might be interested in finding all patients with aortic valve disease. The reference terminology creates links between "medical concepts" that allow these types of data queries.

One method of managing these various terminologies may involve generating an interface terminology configured to capture each user's clinical intent. The reference terminology may include a plurality of domains (problem, plan, medication, etc.), a plurality of unique concepts within each domain, and one or more descriptions mapped to each concept, where each description represents an alternative way to express a concept, and where each description captures various users' clinical intent. Exemplary methods for managing multiple terminologies through the use of an interface terminology may be found in the commonly owned U.S. patent application Ser. No. 13/660,512, the contents of which are incorporated herein by reference.

While EHRs aggregate patient information into a single location, they may suffer from information overload. For example, an EHR may include a patient problem list. Every time the patient indicates that he or she has a problem, that problem may get added to the patient list, causing the list to grow. Other types of additions include automated additions or additions to the problem list from multiple caregivers given access to modify the same list. Over time, this list may contain many entries, including duplicate problems, inaccurate problems, and outdated or resolved problems.

Similarly, because the problem list includes all of the patient's stated problems, it may contain information that, while current and unique, may not be that useful to the practitioner, particularly when the practitioner is a specialist. At the same time, the problems that actually are most useful to the practitioner may be overlooked or otherwise missed when the practitioner is reviewing the entire problem list.

In addition, while one of the benefits of an EMR is record portability, difficulties may arise when problem lists from multiple sources are combined, particularly if those lists come from different types or formats of EMRs, or contain problems that are represented within multiple different reference vocabularies.

What are needed are a system and method that address one or more of the issues presented above in order to present a clearer picture of the patient's problems.

BRIEF SUMMARY OF THE INVENTION

In one aspect, a method for generating a user interface for analyzing a patient-specific electronic medical record or an electronic health record that includes a problem list with one or more problems selected from among a plurality of potential problems includes the steps of grouping related potential problems into one or more problem list categories and grouping a subset of the related potential problems into one or more clusters within the one or more problem list categories. The method also includes the step of mapping, using a computer, entries in a problem list with a respective description in an interface terminology, where the interface terminology comprises a plurality of domains, a plurality of concepts, and a plurality of descriptions, where each concept is unique within a given domain, and where each description maps to a respective concept in the interface terminology and is an alternative way to express the respective concept. Additionally, the method includes associating one or more of medication, lab result, procedure, imaging, or allergy data in the electronic medical record or electronic health record with at least one problem. A user request corresponding to a problem or a problem list category is received. Medication, lab result, procedure, imaging, or allergy data contained in the electronic medical record or electronic health record and associated with the requested data by virtue of being grouped in a cluster with the requested data is identified. And a user interface is modified to display the identified data separate from other medication, lab result, procedure, imaging, or allergy data included in the electronic medical record or electronic health record.

In another aspect, a method for generating a user interface for analyzing a patient-specific electronic medical record or an electronic health record that includes a problem list with one or more problems selected from among a plurality of potential problems includes the steps of grouping related potential problems into one or more problem list categories and grouping a subset of the related potential problems into one or more clusters within the one or more problem list categories. The method also includes the step of mapping, using a computer, entries in a problem list with a respective description in an interface terminology, wherein the interface terminology comprises a plurality of domains, a plurality of concepts, and a plurality of descriptions, where each concept is unique within a given domain, and where each description maps to a respective concept in the interface terminology and is an alternative way to express the respective concept. Additionally, the method includes associating one or more of medication, lab result, procedure, imaging, or allergy data in the electronic medical record or electronic health record with at least one problem. A user request corresponding to medication, lab result, procedure, imaging, or allergy data is received. Medication, lab result, procedure, imaging, or allergy data other than the requested data is identified, the identified data contained in the electronic medical record or electronic health record and associated with the requested data by virtue of being grouped in a cluster with the requested data. And a user interface is modified to display the identified data separate from other medication, lab result, procedure, imaging, or allergy data included in the electronic medical record or electronic health record.

In still another aspect, a method for identifying patient-specific care plans through a patient-specific problem list in an electronic medical record or an electronic health record includes the steps of mapping, using a computer, entries in a problem list with a respective description in an interface terminology, where the interface terminology comprises a plurality of domains, a plurality of concepts, and a plurality of descriptions, where each concept is unique within a given domain, and where each description maps to a respective concept in the interface terminology and is an alternative way to express the respective concept, analyzing, by a computer, interface terminology concepts mapped to each mapped entry to determine related problem list entries, and grouping related entries into one or more problem list categories. The method also includes, for each problem in a problem list category, identifying one or more care plans triggered by the problem, and for each problem list category, aggregating the one or more care plans triggered by each problem in that category into one or more types of care plans. Additionally, the method includes accessing a user profile stored on a computer and displaying each type of care plan in separate regions of the graphical user interface, each region including a unique header wherein the regions are dynamically arranged in the user interface in accordance with the user profile.

The care plans may include one or more medications, which may encoded with an RxNorm code. Additionally or alternatively, the care plans may include one or more laboratory tests, which may be encoded with a Logical Observation Identifiers Names and Codes (LOINC) code.

Problem list elements already may be tagged or coded with one or more terminologies, including administrative, clinical, and reference terminologies. The method may include determining a mapping between these terminologies and interface terminology concepts in order to determine which interface terminology concepts apply.

Features and advantages are described in the following description, with reference to the accompanying drawings.

BRIEF DESCRIPTION OF THE SEVERAL VIEWS OF THE DRAWINGS

FIG. 2 is a depiction of exemplary relationships between problem list elements within a clinical category and an example of how problems can be nested together or seen in full detail.

FIG. 3 is a depiction of problem lists from different sources, illustrating differences in the way in which problem list elements are arranged and displayed.

FIG. 4 is a depiction of the reconciliation of elements of multiple problem lists into a single, unified list.

FIG. 5 illustrates two separate problem lists side-by-side, the lists requiring reconciliation, but the entries in the lists being seemingly rather different from one another.

FIG. 7 is a depiction of a reconciled problem list created from the two lists in FIG. 5 using the methods described.

FIG. 16 is an example of a dynamic user interface for implementing the methodology of FIG. 8.

FIG. 17 is an example of the dynamic user interface of FIG. 16 with its display areas modified to reflect a user selection of a patient's vital labs.

FIG. 18 is an example of the dynamic user interface of FIG. 16, with its display area modified to reflect a user selection of a specific category of problems, and its medications, lab results, and procedures regions being modified to generate category-specific displays within those regions.

FIG. 19 is an example of the dynamic user interface of FIG. 16, with its display area modified to reflect a user selection of a different specific category of problems, and its medications, lab results, and procedures regions being modified to generate category-specific displays within those regions.

FIG. 20 is an example of the dynamic user interface of FIG. 16, with its display area modified to reflect a user selection of a specific problem within the category of problems selected in FIG. 19, and its medications, lab results, and procedures regions being modified to generate problem-specific displays within those regions.

FIG. 21 is an example of the dynamic user interface of FIG. 16, with its display area modified to reflect a user input of a specific problem not contained within the problem list section of that interface and with its medications, lab results, and procedures regions being modified to generate problem-specific displays within those regions.

DETAILED DESCRIPTION

Figure 1:
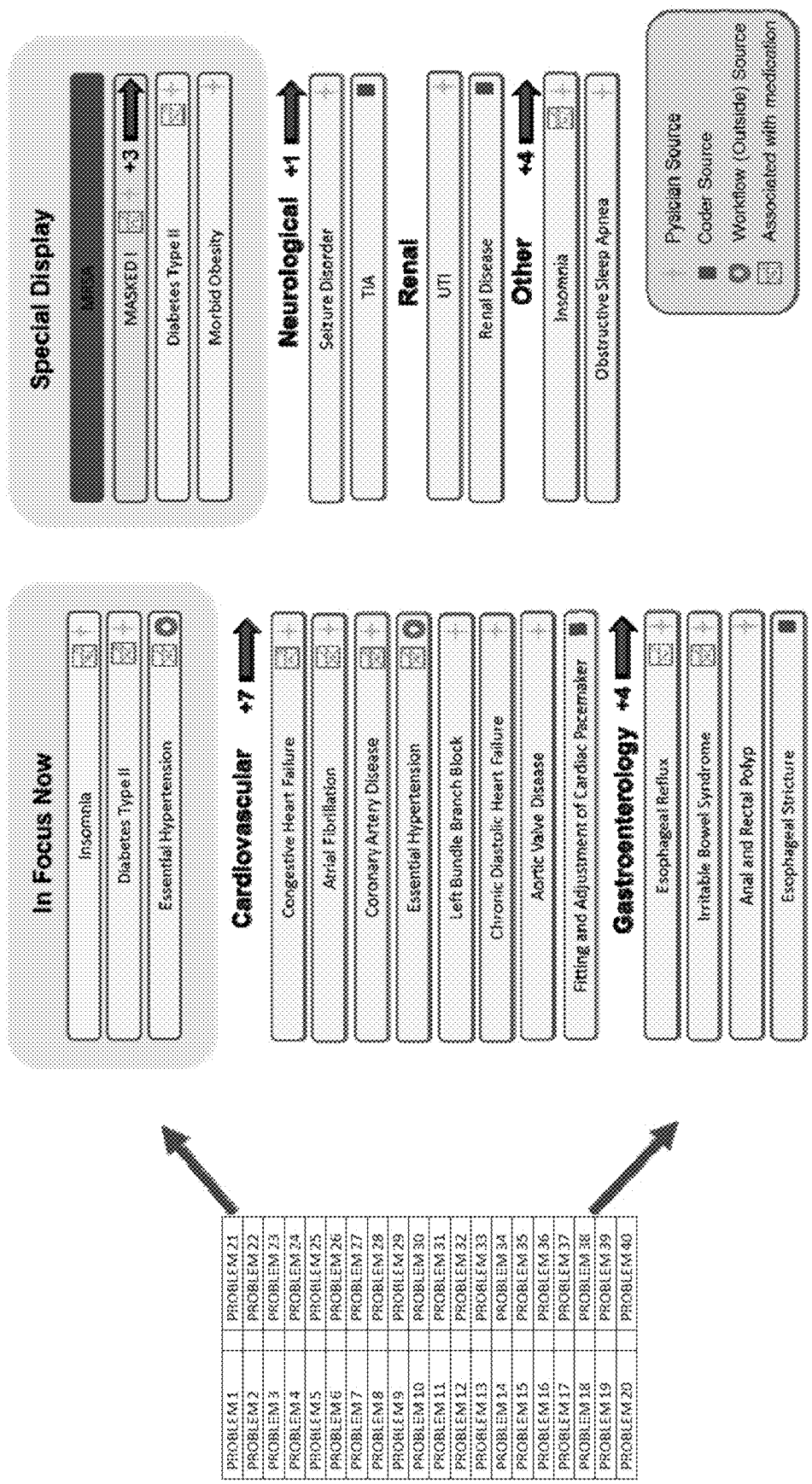
FIG. 1 is a depiction of a method of reconciling a general problem list into one or more clinical categories based on concept groupings. In this case the concept group is related to clinical specialties such as Gastroenterology or Cardiovascular. Many different concept groupings can be enabled using the methods described.

As seen in FIG. 1, a method for processing electronic medical record problem lists may be employed to generate a clinically relevant patient profile. In one aspect, the patient profile may be useful to a clinician because it may categorize and group related problems according to concept groupings, and groupings may be determined based on semantic distance between the represented concepts. For example, all cardiovascular problems may be grouped under a "cardiovascular" category, all kidney-related problems may be grouped under a "renal" category, etc.

In addition, the system may attach indicator flags to the problems within each category, which may permit later ranking and ranked display of the problems according to attributes, such as severity, timeliness, or other concepts such as classification within a clinical measure. One example of such a flag is seen in FIG. 2, in which the problem "Diabetes mellitus" and the related problems clustered underneath that summary problem are marked with a CQM flag. The system may apply an indicator flag to the summary problem if any of its clustered problems (as that term is discussed in greater detail below) include the flag.

The CQM, i.e., Clinical Quality Measurement, flag indicates that its associated problem element must comply with CQM requirements for treatment and documentation in order to be eligible for the reimbursements provided for such compliance. Thus, a problem having this flag may be presented to the user as a higher value or higher priority problem element. In addition to having the flag callout, this flag also may be used as a factor in problem list ranking. For example, CQM problems may be ranked and presented higher on the problem list within each category than other, non-flagged problem elements.

Other potential flags may include HCC (Hierarchical Condition Category), CC (Complication and Comorbidity), and MCC (Major Complication and Comorbidity). One of ordinary skill in the art would appreciate that values associated with these terms are reflective of the severity of their underlying problems. As such, problems flagged with one or more of these flags may provide a visual indicator to the user that they may need to be addressed with higher priority than other problems on the list.

Returning to FIG. 1, multiple criteria in addition to the indicator flags may be applied to the problems in order to determine the rankings within these lists. For example, problems that are associated with/require medication may be ranked higher than those that are/do not. Problems that are entered by a physician/clinician may be ranked higher than those that are sourced from other entities later in the record review process, e.g., by a coder or other administrative personnel. Problems that are obtained from workflow or some other outsider source, e.g., those problems that may be extracted from review of the patient's chart may rank somewhere in between clinician- and coder-generated problems (assuming all other factors are the same). Problem entries may be time-stamped, such that more recent problems may be ranked higher than older problems.

The clinicians viewing the problem list then can see the problems that pertain to their specialty quickly and easily, e.g., a cardiologist can look for the cardiovascular category and then focus on its entries. In one aspect, the clinician may be able to set up a filter to display preferred problems or categories of problems, while excluding non-selected problems or categories from being displayed. In another aspect, clinicians may pre-establish a profile that includes details about their preferred practice area(s). Upon logging-on to the system, the clinician's personal information may be retrieved. When the clinician selects a patient's record, the system then may cross-check the clinician's profile with each of the categories of problems. The system then may display one or more problems or categories of problems that match that clinician's profile. In either case, the filter may function to bring a specialty-based problem view to the front of the clinician's review.

Other filters may include the option to show an expanded list that shows every problem in a category vs. a summary or nested list that shows the highest level problem for a group of problems within a category, with the other problems being closed off or otherwise hidden from view.

The system also enables identification of potentially sensitive problems, so that the EHR can mark them for special treatment such as a secondary layer of privacy for viewing, or special attention by the clinician who has access to the Problem List. Examples of "sensitive" problems include, e.g., HIV and mental illness. Marking a problem as sensitive may allow it to be masked from some users, thereby restricting access only to those who are authorized.

The system also may generate lists in order to call attention to problems that may require more immediate attention or problems that may affect multiple disciplines. For example, another possible category may be an "in focus now" category, which may display those problems currently most relevant to the user, regardless of whether the problem also can fit into one of the other categories described above, and a "special display" category, which may list high priority problems of extreme, immediate importance, or of problems which are always part of the patient's overall baseline health state. These problems may be categorized more specifically, but they may have effects that cross disciplines, such that the clinician may desire to know about them when addressing the specific problems within his or her discipline.

In another aspect, it may be desirable to refine the problem list by eliminating redundancies or categorizing which problems are resolved vs. which ones are chronic or ongoing, etc. The same or similar ranking criteria as those described above with regard to problem entries within each category may be applied to the problem list as a whole in order to rank the entries, regardless of categorization. Alternatively, the category that may apply to a particular problem also may serve as a criterion in this ranking analysis, e.g., a cardiac or neurological problem may be ranked higher than an orthopedic one.

The system may display or output each tagged problem using description elements within the interface terminology, i.e., alternative ways to express the concept, because this may better express clinical intent, particularly the intent of the entity that created the problem/added the problem to the patient's list.

The system also may include a map between the various concepts within the interface terminology and with elements of other, external terminologies and vocabulary datasets, such as ICD9, ICD10, SNOMEDCT, MeSH, and Clinical Quality Measure elements, etc. These mappings may be precompiled such that the system may avoid needing to remap relationships between interface terminology elements and the external sets when dealing with additional problem lists, e.g., the lists of other patients.

This mapping may serve as the basis for the categorization, grouping, rolling up, nesting, etc., of the entries in a problem list. Certain interface terminology concepts may be related to other interface terminology concepts based on similar subject matter. For example, there may be a plurality of concepts that pertain to cardiac conditions. Thus, all problems that map to these concepts may be grouped together for categorization and display such as that shown in FIG. 1.

In addition to the ranking or sorting criteria describe above, these outside vocabulary mappings may be an additional factor used to rank the problem list entries. For example, mappings to some established terminologies or vocabularies may be used to perform the mapping/grouping described in the previous paragraph, and mappings to a second terminology or vocabulary or a proprietary mechanism may be used to sort more specifically within the determined categories.

Turning now to FIG. 2, it will be seen that certain problems not only fall within the same category as other problems but that they also may be considered subsets of another problem, i.e., they may be clusters within that problem. These relationships can be determined and managed by using the interface terminology, which also may recognize that certain concepts are more general than others and thus are hierarchically related to those other concepts. The system may group these more specific concepts underneath the more general, parent concept, thereby further arranging the problem list, whose entries may be mapped to these sub-concepts. As it relates to presentation of these problem list entries, the system may display in the problem list the problem that maps to the more general, parent concept and an indicator that other problem entries are nested or clustered and may be viewable under that parent problem, e.g., by clicking on the indicator.

In one aspect, clustered problem elements underneath a more general, parent concept may be ranked or organized using one or more of the criteria discussed above for ranking elements within the problem list generally. Alternatively, as seen in FIG. 2, clustered problem elements may be arranged using a more simplistic algorithm, e.g., they may be arranged alphabetically. In still another aspect, the system may rank flagged problems above non-ranked problems and then apply the more simplistic algorithm within each of those subsets. In any event, the system may allow user customization, permitting the user to rearrange the ordering of elements both in the problem list and within the clustered subsets, as discussed below.

From a database management perspective, clustered problems may be stored as a list of elements in a flat file database, with each element pointing to its parent problem element. Alternatively, clusters may be sub-trees in a hierarchical database structure underneath their respective category elements.

To this point, the patient list has been described as being patient specific, i.e., each patient has his or her own list, with entries specific to that patient in order to accurately record the patient's problem history. The system and method may function similarly as a way to bring a clearer clinical picture for a population aggregator, i.e., determining what problems exist for a given population, or for a given patient who may have multiple problems culled from multiple sources within a large data warehouse. In that case, the number of problems in the aggregated list may be larger (likely significantly larger) than for an individual record within an EHR, although the methodology may remain the same, i.e., each problem may be mapped to an interface terminology concept, concepts may be grouped and ordered, and the ordered problems then may be available for logical display and analysis.

As seen in FIG. 3, and as discussed above, another issue with problem lists may become evident when attempts are made to combine lists from multiple different sources. These sources may format, store, and/or represent elements in the list differently from one another and not in a consistent format.

In order to accomplish reconciliation of elements within a single list (i.e., grouping problems within a list into categories and establishing clusters within those categories, which may or may not include the step of combining elements from multiple problem lists into a single list), the system may create an anchoring term from an interface terminology foundation technology that permits creation of a semantic distance between any two other terms from external vocabularies. This anchoring term may be considered a central concept within an interface terminology. In one aspect, determining this anchoring term may be achieved by a concept tagging method, and examples of such a method may be found in the commonly-owned co-pending U.S. application Ser. No. 13/004,128, the contents of which also are incorporated by reference.

For example, the process may comprise populating a database with a plurality of distinct concepts, populating a database with a plurality of descriptions, relating each description to a respective concept, reviewing the content (e.g., the problem list elements) for a satisfactory description match; and creating a tag for the satisfactory description match. Concepts may be well-defined clinical findings, i.e., items that are distinct by nature. Descriptions may comprise a plurality of words. Factors for determining whether the match is satisfactory may include whether there is a textual match between a portion of the content and the description and a distance between words in the content, the words corresponding to discrete words of each description.

Each concept may be part of a tree or hierarchy of other concepts, i.e., each concept preferably may have, at most, one parent concept, although it also may have multiple child concepts. A "Knee Pain" concept (term) may be expanded semantically to parent/child clinical concepts, including semantic distance that will help build the problem list ranking. For example, knee pain may be connected up to the broader concept of joint pain, which may be connected to musculoskeletal pain. Similarly, knee pain may be connected down to the more specific concepts of anterior knee pain and knee joint, painful on movement. This semantic difference may be expressed in terms of discrete positive or negative values away from the concept.

The heuristic that determines a problem's final ranking may be a function of description frequency and description presence factor, as well as the semantic difference or distance from other descriptions. Because multiple descriptions may relate to a shared concept, description frequency may be a compound value of all occurrences of all description variances of a shared concept, here, e.g., the concept of "Knee Pain." Relatedly, a term presence factor may reflect how "close" or "loose" a potential concept match may be. For example, the phrase "knee pain" may have a high term presence factor for the concept "knee pain," whereas the phrase "pain under kneecap" may have a lower term presence factor, reflecting the difference in terminology and inference that is required to make the match.

Thus, each problem list element is analyzed and tagged with a description that represents the clinical intent behind that element, the description being part of an interface terminology and mapping within that terminology to a concept, thereby normalizing the problem list elements. The problems then may be analyzed, using those concept tags, to determine if any relationship exists among them, e.g., whether they represent duplications or related concepts (broader than/less than/subset of), or whether they are unrelated. Once analyzed, the elements may be grouped and ranked as described above, for presentation to and review by the user.

Turning now to FIG. 4, the method may include incorporating and reconciling problem lists from multiple sources, e.g., from multiple EHR sources or from an EHR and from a Consolidated Clinical Document Architecture (CCDA) source. This latter case may be particularly useful in order to comply with Meaningful Use, Stage 2 (MU2) requirements, which require the ability to incorporate and reconcile an inbound CCDA problem list with the home EHR list. In still another example, the secondary list needing reconciliation may be generated by Natural Language Processing (NLP) suggestions.

As with a single problem list, the final product may be an ordered, categorized, clinical problem list. In addition to this ordering, however, the system may determine and reconcile conflicts or redundancies between multiple lists. Reconciliation may require the steps of: identifying which problems are identical; identifying which problems are closely related; and creating a mechanism to incorporate, preferably rapidly and accurately, reject, or refine both sets of problems into a new clinical set.

In this aspect, tools similar to those described above may be used to reconcile the multiple problem lists. For example, problems in each list may be tagged using a common interface terminology. Once this commonality has been established, the entries from the two lists may be combined into a single list using the interface terminology mappings as a guidebook.

One advantage of this type of reconciliation is that one of the two lists already may include mappings between the problems and some kind of code set. For example, the CCDA-structured problem list that complies with MU2 may have its problems coded with SNOMED-CT codes. As such, the analysis of the problems in that list may be simplified, because it may be easier to map the SNOMED-CT codes to interface terminology concepts than to do a mapping between the text of the problem and the interface terminology.

In addition, while this automated procedure may be able to reconcile problem lists with a high degree of accuracy and completeness (e.g., between about 90% and about 95%), the system may benefit from a human interaction component. As such, the system may include a package of refinement tools that may permit a user, e.g., a clinician that has the experience and knowledge, to evaluate potentially similar entries and determine what, if any, relationship might exist between those entries. For example, the user may be able to move an entry from one category into another, from no category to an existing category, or from an existing category into either a new category or into an undefined area. The user also may able to move the entry around within the category, e.g., moving it up or down to reflect a higher or lower priority, respectively, or determining that it belongs as a subentry of an already-existing problem.

Figure 6:
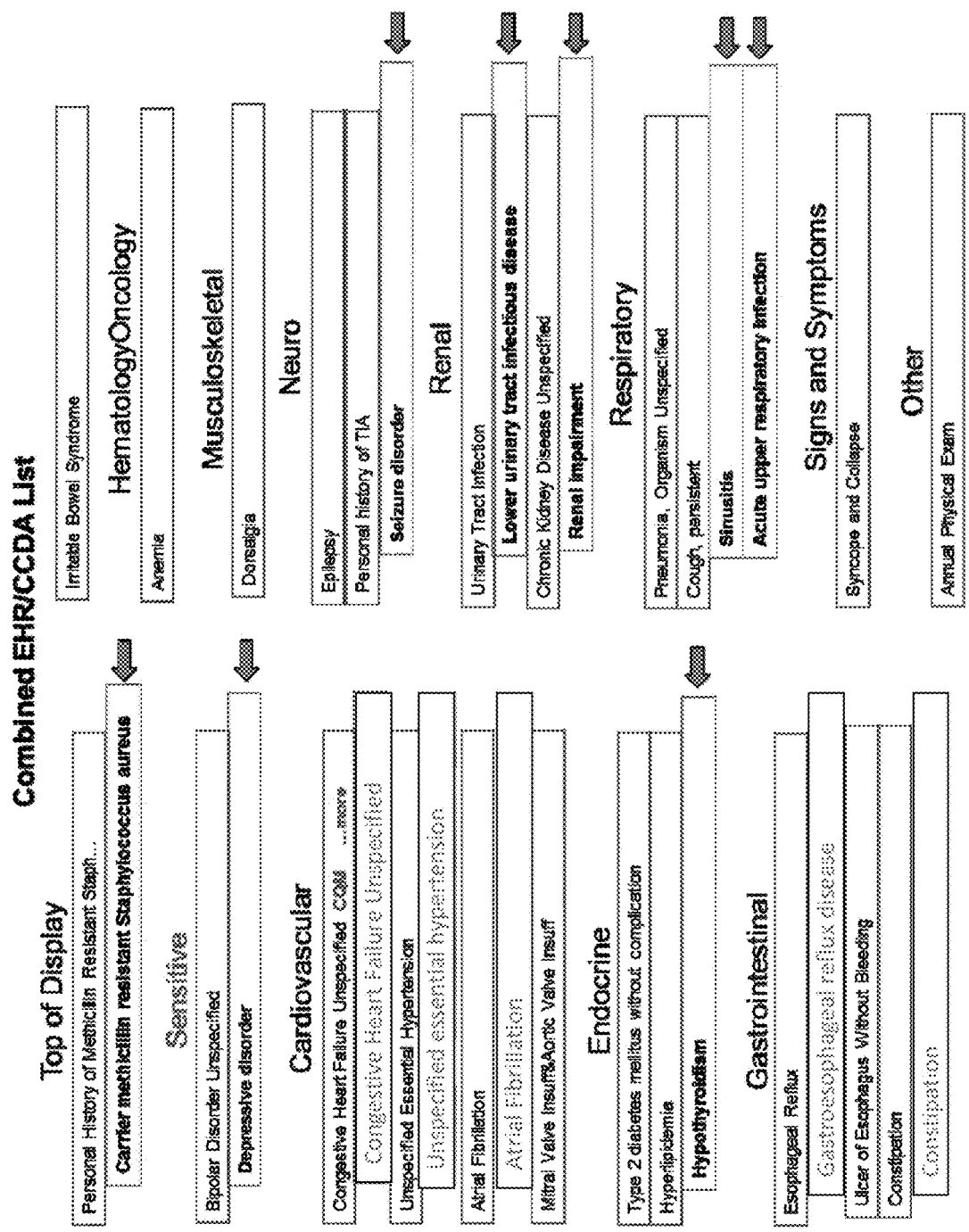
FIG. 6 illustrates the two lists mapped on top of one another, with duplicates highlighted in a first fashion and non-duplicates highlighted in a second fashion.

FIG. 5 shows one example of two lists for reconciliation side-by-side, e.g., an EHR list and a CCDA list for import. FIG. 6 then shows a presentation layer implementing one example of the reconciliation strategy. This presentation layer depicts the entries from the EHR as the left-justified items and the CCDA entries as the right-justified items. In addition, the system analyzes the data sets to determine whether, once the problems have been mapped to the interface terminology concepts, there are any duplicates. If so, the presentation layer may alert the user to the existence of the duplicates, e.g., by locating the duplicate next to the problem it matches and by graying it out or otherwise indicating that it should remain in that location and not be moved elsewhere.

In addition, the system may flag non-duplicates, e.g., with the indicator arrows shown in FIG. 6. As can be seen, the system already automatically may have determined that the non-duplicates belong in certain categories. In this case, the presentation layer may be used by the user to move the non-duplicates, either within the categories in which they were placed or to a different category altogether.

Turning now to FIG. 7, a reconciled problem list is shown, with the multiple lists combined into a single, comprehensive problem list. New entries may be shown in boldface or otherwise may be highlighted to alert the user to the additions. In addition, different term sets may be used on the problem list and may be presented to the user. In one aspect, the system may display the problems using the interface terminology concept labels that were applied to the problem entries. However, the system may also give the user an option to display the terms as they appeared in the lists prior to reconciliation, as those terms may more accurately reflect the clinical intent of the individual that generated the problem. In that case, the interface terminology mapping may remain in the background, such that the interface terminology terms may not be exposed to the end users.

The system may function as a separate widget or application accessible by an EHR software package. Preferably, however, this problem list analysis and reconciliation tool may be integrated into the EHR package.

In still another aspect, the system may recognize that certain combinations of problems may trigger one or more care plans. Thus, the system may analyze the various problem list entries to determine whether care plans are recommended and if so, which ones. This analysis may be performed using the interface terminology concepts tagged to each problem list element, which may increase processing efficiency since a comparison between those existing concepts and the various care plans may be precompiled and only may require, e.g., a simple table lookup, instead of requiring analysis and evaluation of non-normalized problem list terms as entered.

In conjunction with the organized problem list, the system then may output and display a care plan callout with indicators referring to the associated problems. For example, each care plan that the system recognizes may be displayed/highlighted/etc. in a distinct color, and the problems associated with a care plan similarly may be highlighted in the same color.

Additionally, depending on the number of problems in the list, the system may determine that multiple care plans are implicated. Thus, the system may rank those care plans, e.g., according to severity, timeliness, or other factors. Factors used in the ranking may include one or more of those discussed above for determining problem list rankings. In addition, the system may analyze the problems that trigger each care plan, using the rankings of those problems as a factor in ranking the care plans.

The system may be extended beyond intelligent analysis of a patient problem list to evaluate other, disparate aspects of a patient's electronic health record and/or to evaluate aspects of a patient's medical history as recorded in multiple records, as when aggregated via a health information exchange. In addition to problem list elements, the system may be configured to analyze and provide an intuitive display of medications, laboratory results, procedures or other treatments, imaging results, past medical history or surgeries, notes, vital signs, allergies, or other medical data associated with diagnoses or specialties from within the problem list. Notably, the system may be configured to assist in providing a differential diagnosis by identifying all relevant past and/or current medications, laboratory results, procedures or other treatments, imaging results, past medical history or surgeries, notes, vital signs, allergies, or other medical data that are related to a problem, whether that problem is recorded in the patient's problem list or not.

Figure 8:
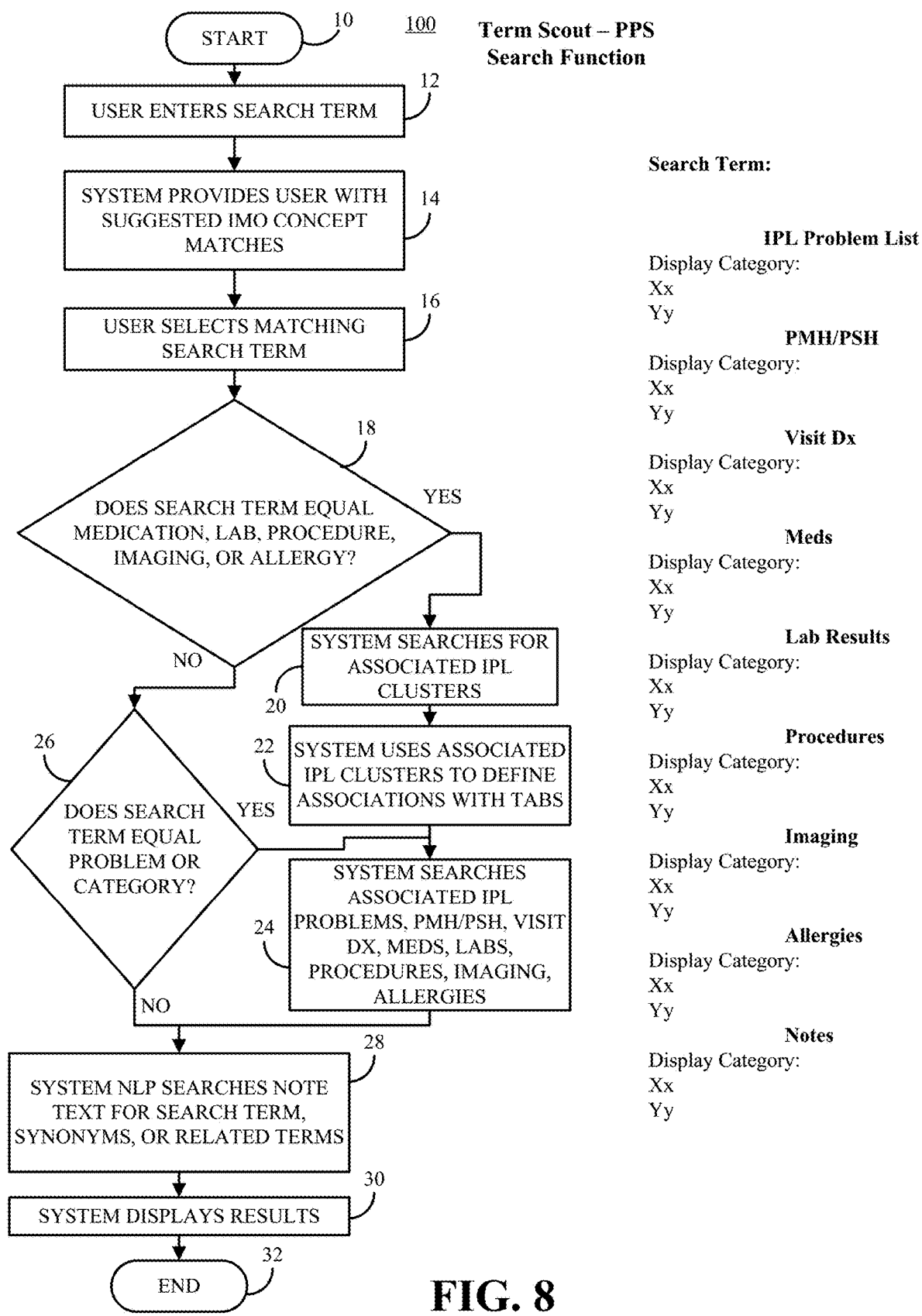
FIG. 8 is a flowchart of a general methodology for analyzing a specific patient's electronic health record to identify various aspects of that record relevant to a user query.

FIG. 8 provides one example of a general search methodology 100 using the disclosure provided herein. Following the start 10 of the method, the method includes the steps of receiving 12 a search term, returning 14 one or more potential interface terminology concepts as matches, and receiving 16 a selection from the user of one of the matching terms. The system then evaluates 18 the user selection to determine if it corresponds to a medication, lab result, procedure, imaging, or allergy, i.e., whether it corresponds to an entry in one of those domains.

If the answer to step 18 is no, then at step 20, the system may determine whether the matched term corresponds to an entry in the problem domain or to a category of problems. If the answer to step 18 is yes, then the method includes the step of searching 22 for clusters of problems associated with the matched term. At step 24, the system may use the associated clusters to define associations. As part of an ultimate display of a dynamic graphical user interface, relevant associations may be presented within various tabs on the display.

At that point, or if the answer to the determining step 20 is yes, the method may include the step of searching 26 the patient's record for relevant problems (including visit diagnoses), medications, labs, procedures or other treatments (including searching past medical history ("PMH") and past surgical history ("PSH"), imaging and/or allergies. Optionally, the method also may include searching 28 unstructured portions of the patient's record (e.g., notes or other text) for the search term, synonyms, or other related terms. Various searching and analysis techniques may be used to make that text usable, including, e.g., natural language processing and mapping between the processed text and concepts or lexicals within the interface terminology.

Once the system has identified the relevant components of the patient's electronic health record, the method includes displaying 30 the results, e.g., by modifying the user interface to include one or more tabs presenting the relevant information. For example, the system may collapse the problem list portion of the interface in order to generate an adjacent tab with relevant medication information and a second adjacent tab with relevant lab information. Alternatively, as described below, the user interface may include separate regions for each type of data in the patient's record, and the preceding steps may be used to reconfigure, reorder, filter, or otherwise modify the data in one or more regions of the display to present it in a way that permits more immediate comprehension and additional analysis of the patient record. At that point, the method then may end, as at step 32.

In order to ensure accuracy of the mappings between problems and medications, labs, procedures, imaging results, past medical history or surgeries, notes, vital signs, allergies, or other medical data, the system may rely on the structuring metadata underlying each piece of information in the electronic health record. In particular, as discussed above, each problem on the problem list may be encoded with a specific identifier from one or more ontologies, including a unique identifier associated with the interface terminology concept to which the problem is mapped. Each problem also may be encoded with a unique identifier from one or more other ontologies, including an administrative terminology such as ICD-10-CM and/or a reference terminology such as SNOMED Similarly, the various other data types also may be encoded with unique codes from one or more other ontologies. For example, each medication may be encoded with a specific RxNorm code, each lab result may be encoded with a specific LOINC code, and each procedure and imaging piece of data may be encoded with its own CPT-4, SNOMED, and/or HCPCS code. Mappings then may occur by linking the relevant codes for the medications, labs, etc., to the codes for their respective problems. Alternatively, each cluster and/or category may have its own unique identifier, and the relevant codes for medications, labs, etc., as well as the relevant codes for each problem may map indirectly to one another via mappings of both the cluster or category identifier.

Figure 9:
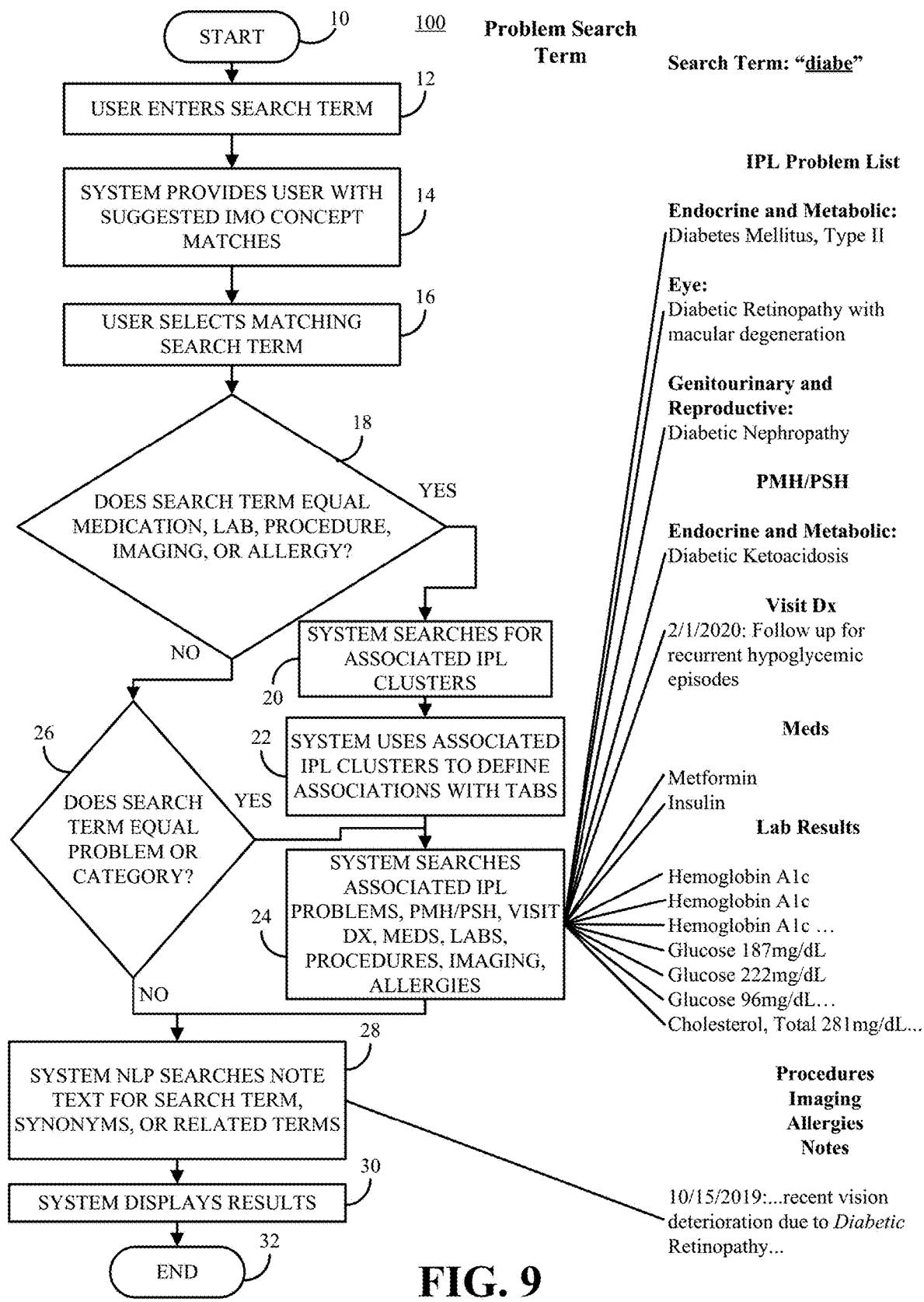
FIG. 9 is an example of the flowchart and analytical methodology of FIG. 8 when the search term corresponds to a medical problem.

FIG. 9 depicts one example of this methodology, in which the user's search most closely resembles a problem list entry. In this example, the user enters the term "diabe," which the system may recognize as mapping to one or more different interface terminology concepts, including, e.g., "diabetes mellitus, Type I," "diabetes mellitus, Type II," "diabetic retinopathy with macular edema," "diabetic retinopathy without macular edema," etc. Upon the user selecting the term "diabetes mellitus, Type II" at step 16, the system may determine at step 18 that the term is not one of a medication, lab, procedure, imaging, or allergy and proceed to step 20 for a similar analysis. Upon determining that the selected term corresponds to a problem or category of problems at step 20, at step 26 the system then may search for all associated problems, PMH and PSH events, visit diagnoses, medications, labs, procedures, imaging, and allergies to identify all related items within the patient's electronic health record.

As discussed above, problems may be grouped into categories of problems with some type of commonality among each category's problems. Exemplary categories may include: Advance Directives and General Health Issues, Allergies and Adverse reactions, Chromosomal and Congenital, Mental Health, Sensitive Personal, Cardiac and Vasculature, Coagulation and Thromboembolic, Endocrine, Metabolic and Lipids, ENT, Eye, Gastrointestinal and Abdominal, Genitourinary and Reproductive, Gravid and Perinatal, Hematology and Neoplasia, Infectious Diseases, Multi-system, Musculoskeletal and Injuries, Neuro, Pulmonary and Pneumonias, Sleep, Skin, Symptoms and signs, Health Encounters, Tobacco, Family History, and Toxicities and Miscellaneous. Searching step 26 may leverage these relationships to identify any problems encoded in the patient's record that share one or more categories with the selected problem. For example, FIG. 9 illustrates a situation where selection of the term "Diabetes Mellitus, Type II" results in the system also identifying the problem "Diabetic retinopathy with macular degeneration" in an "Eye" category and the problem "Diabetic Nephropathy" in a "Genitourinary and Reproductive" category. The system may perform a similar analysis for PMH/PSH entries within categories of which the selected problem is a part. For example, staying with FIG. 9, the system may identify the PMH/PSH "Diabetic Ketoacidosis" in an "Endocrine and Metabolic" category.

Similarly, visit diagnoses, medications, lab results, procedures, imaging results, and allergies may be cross-mapped with one or more problems to which they may apply, regardless of whether those problems actually appear in the patient's electronic health record or not. Additionally, within the defined categories (such as the ones identified in the preceding paragraph), the system further may group subsets of problems into clusters. This further level of specificity, as compared to the problem categories, may allow the results to be more narrowly tailored in order to provide the user with useful information while at the same time avoiding aggregating too many problems that would lead to an overinclusion of information, thereby reducing the efficacy of the user interface and the user's ability to quickly identify and process relevant information. For example, almost every exemplary category identified above may include at least one infectious disease as a problem within that category. If the medication "amoxicillin" were evaluated at a category level, it is likely that that medication would be mapped to a majority of those infectious diseases. Thus, if this analysis were done at a category level, the system may return not only the relevant infectious diseases, but also every other problem that was part of a category to which any of those diseases was mapped. By creating clusters within the categories, the system may permit the compartmentalization of problems to mitigate this risk. For example, within the Genitourinary and Reproductive category, a "Urinary Tract Infection" cluster may be created, with amoxicillin mapped to that cluster and not to other clusters (and, therefore, other problems) within the Genitourinary and Reproductive category.

Once this pre-processing has been done, then the system at searching step 26 may analyze the patient's record to determine whether it contains any visit diagnoses, medications, lab results, procedures, imaging results, and/or allergies that are cross-mapped to the selected problem or any problem mapped to a cluster to which the selected problem belongs. For example, staying with FIG. 9, the system may identify a 2/1/2020 Visit Dx for "Follow up for recurrent hypoglycemic episodes," the medications "Metformin" and "Insulin," and multiple Hemoglobin A1c, Glucose, and Cholesterol lab results.

At step 28 in FIG. 9, the system then may process unstructured portions of the patient's record to identify instances of the search term, synonyms thereof, or related terms. In this example, natural language processing techniques or other techniques as would be appreciated by those of ordinary skill in the relevant art may be used to identify a 10/15/2019 patient note relating to "recent vision deterioration due to Diabetic Retinopathy."

Once each of these pieces of the patient's electronic health record have been identified, the system may generate a user interface, e.g., modifying a display of the patient's problem list, to present the information to the user, as discussed in greater detail below.

Figure 10:
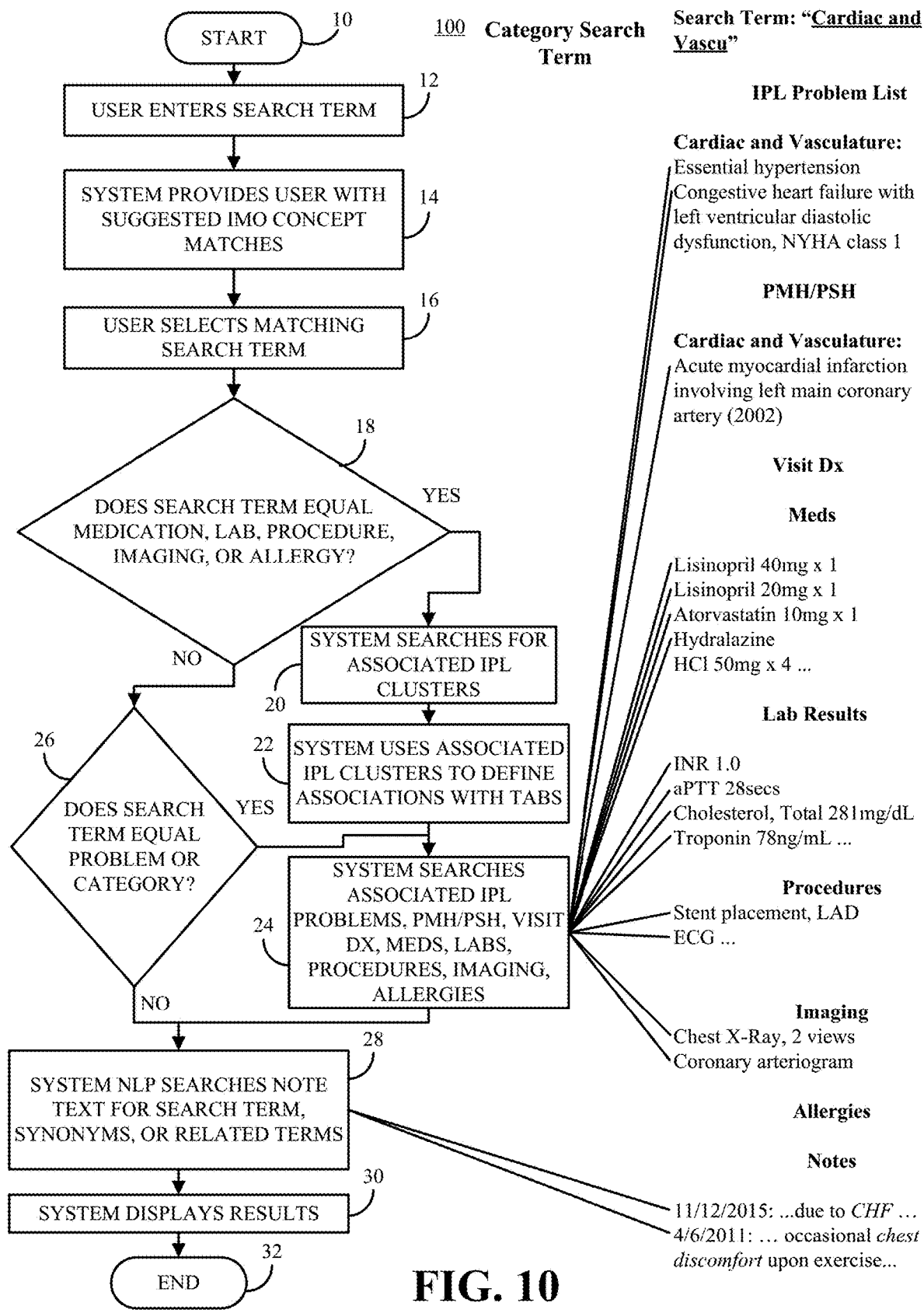
FIG. 10 is an example of the flowchart and analytical methodology of FIG. 8 when the search term corresponds to an identifier of a category of medical problems.

FIG. 10 depicts a second example of this methodology, but where the search term, or the user's selection of a match to the search term, represents one of the categories of problems such as those described above. For example, the user's search term "Cardiac and vascu" may result in the user selecting a matching term corresponding to the category "Cardiac and Vasculature." From there, the method may proceed in a fashion similar to that of the example of FIG. 9 except that, with regard to the problem list and PMH/PSH entries, the system may constrain itself solely to problems and PMH/PSH entries within that selected category.

Figure 11:
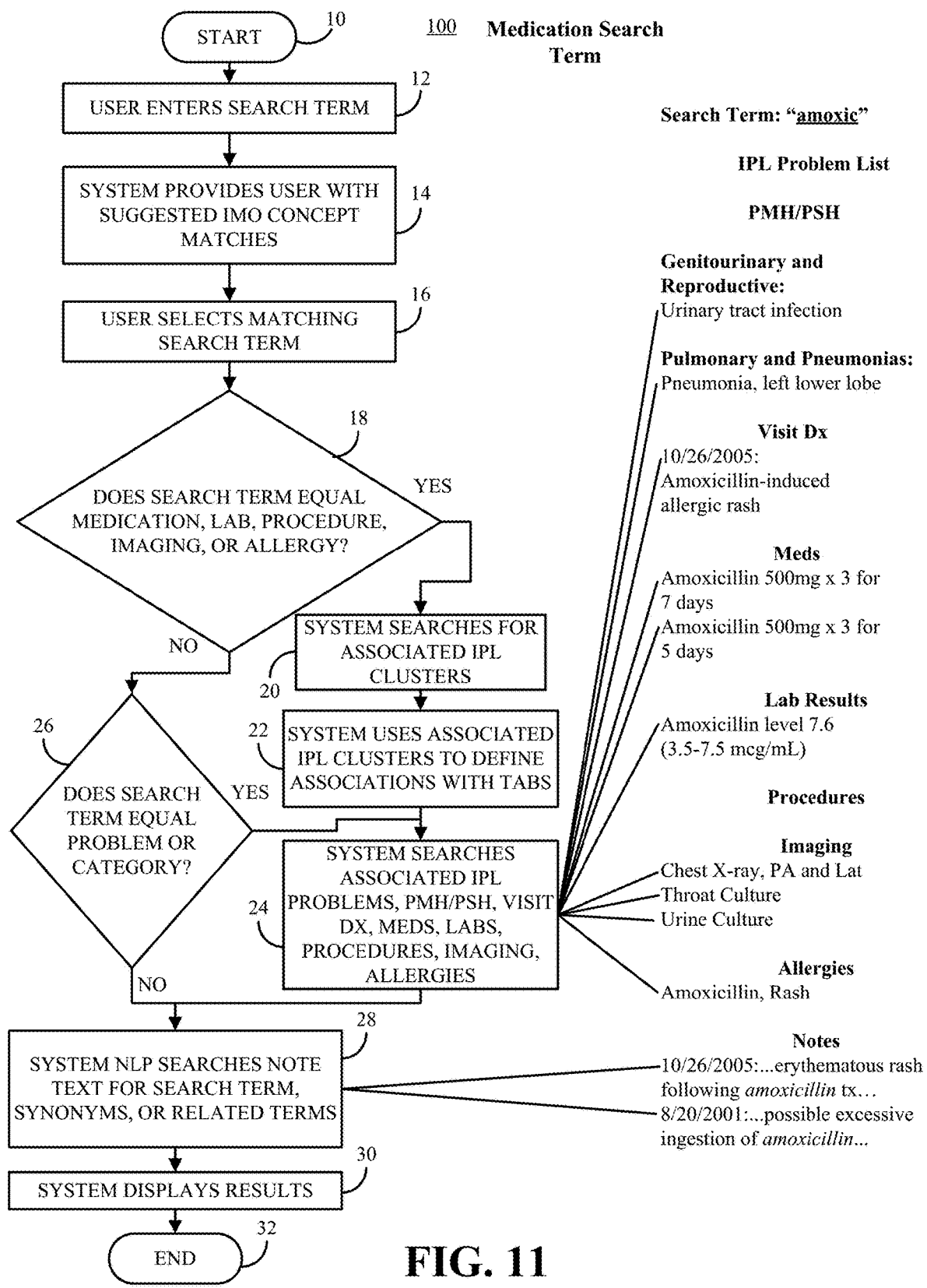
FIG. 11 is an example of the flowchart and analytical methodology of FIG. 8 when the search term corresponds to medication-related information.

FIG. 11 depicts a third example of this methodology, but where the search term, or the user's selection of a match to the search term, represents a medication. For example, the user's search term "amoxic" may result in the user selecting a matching term "amoxicillin."

Figure 12:
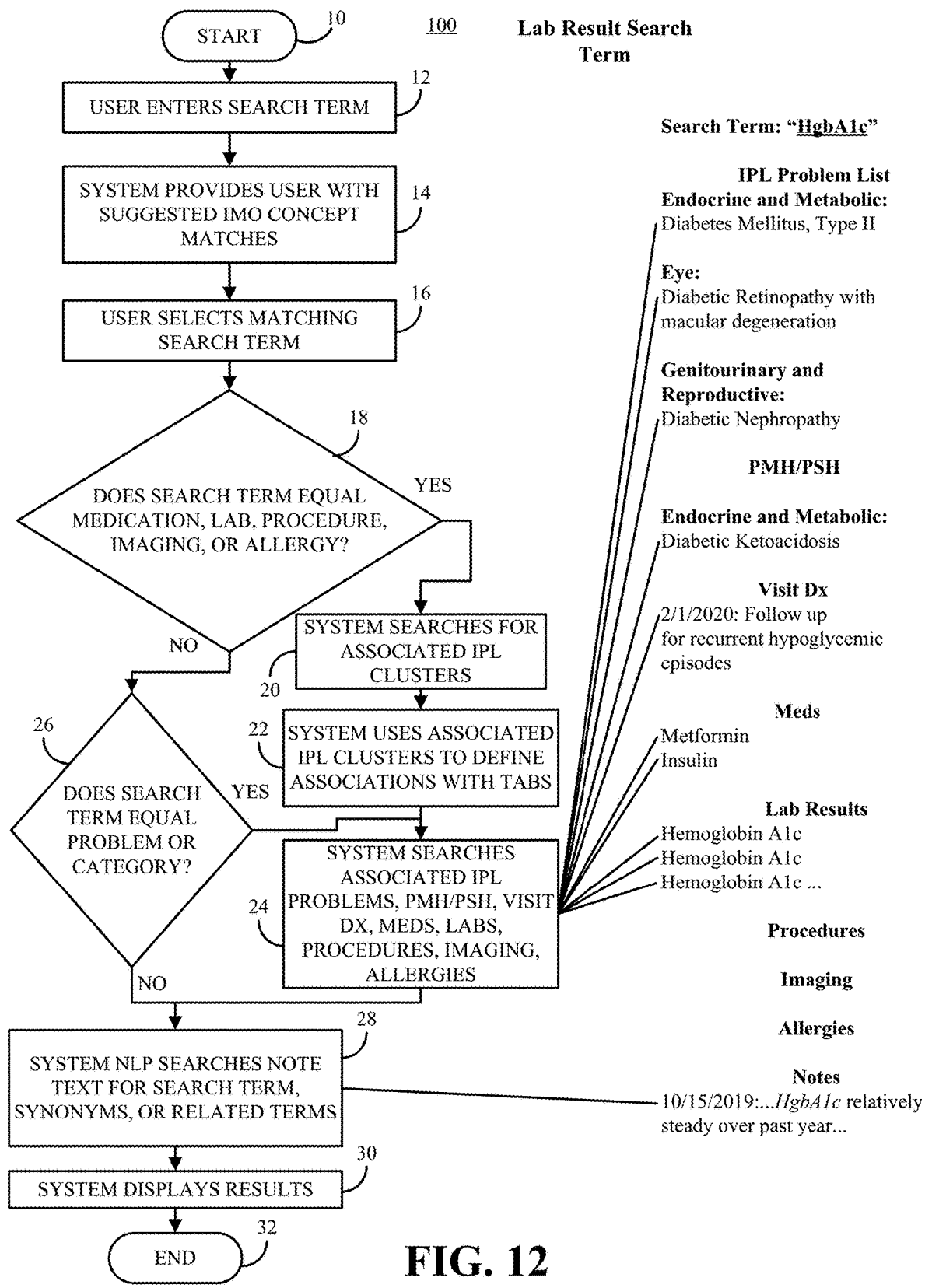
FIG. 12 is an example of the flowchart and analytical methodology of FIG. 8 when the search term corresponds to laboratory result-related information.

FIG. 12 depicts a fourth example of this methodology, but where the search term, or the user's selection of a match to the search term, represents a lab result. For example, the user's search term "HgbA1c" may result in the user selecting a matching term "Hemoglobin A1c."

Figure 13:
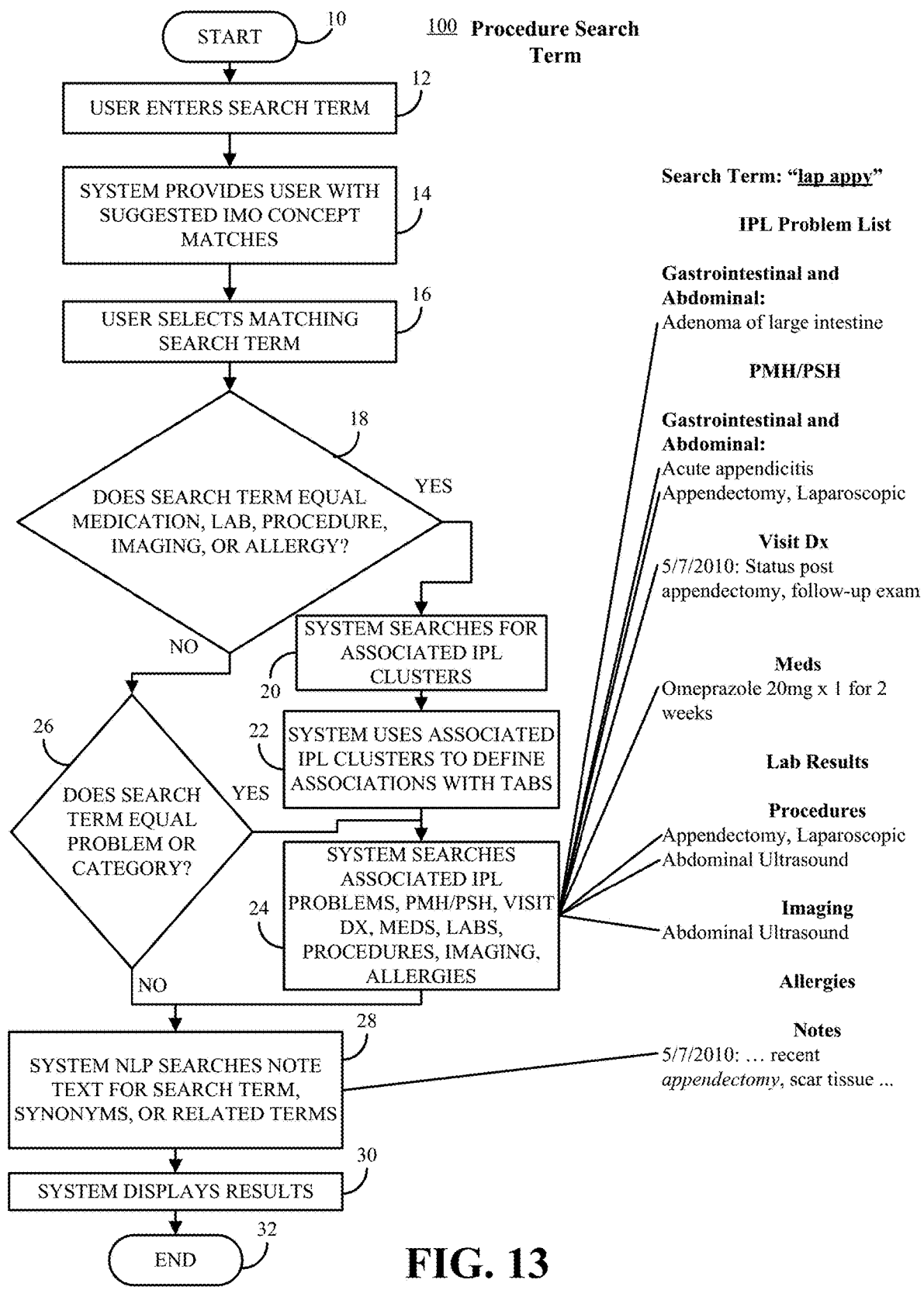
FIG. 13 is an example of the flowchart and analytical methodology of FIG. 8 when the search term corresponds to procedure-related information.

FIG. 13 depicts a fifth example of this methodology, but where the search term, or the user's selection of a match to the search term, represents a procedure. For example, the user's search term "lap appy" may result in the user selecting a matching term "appendectomy, laparoscopic."

Figure 14:
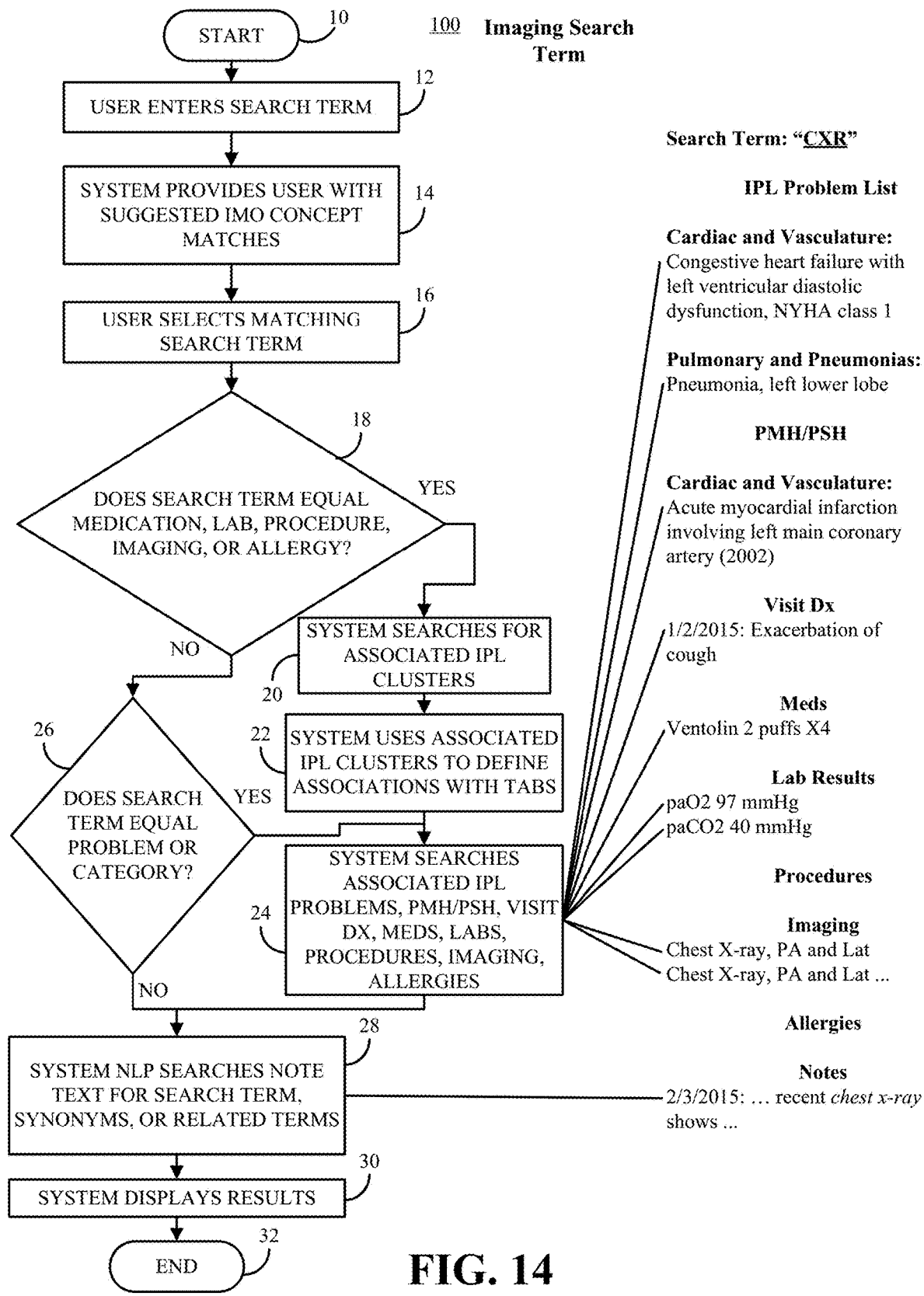
FIG. 14 is an example of the flowchart and analytical methodology of FIG. 8 when the search term corresponds to medical imaging-related information.

FIG. 14 depicts a sixth example of this methodology, but where the search term, or the user's selection of a match to the search term, represents an imaging record. For example, the user's search term "CXR" may result in the user selecting a matching term "chest x-ray."

Figure 15:
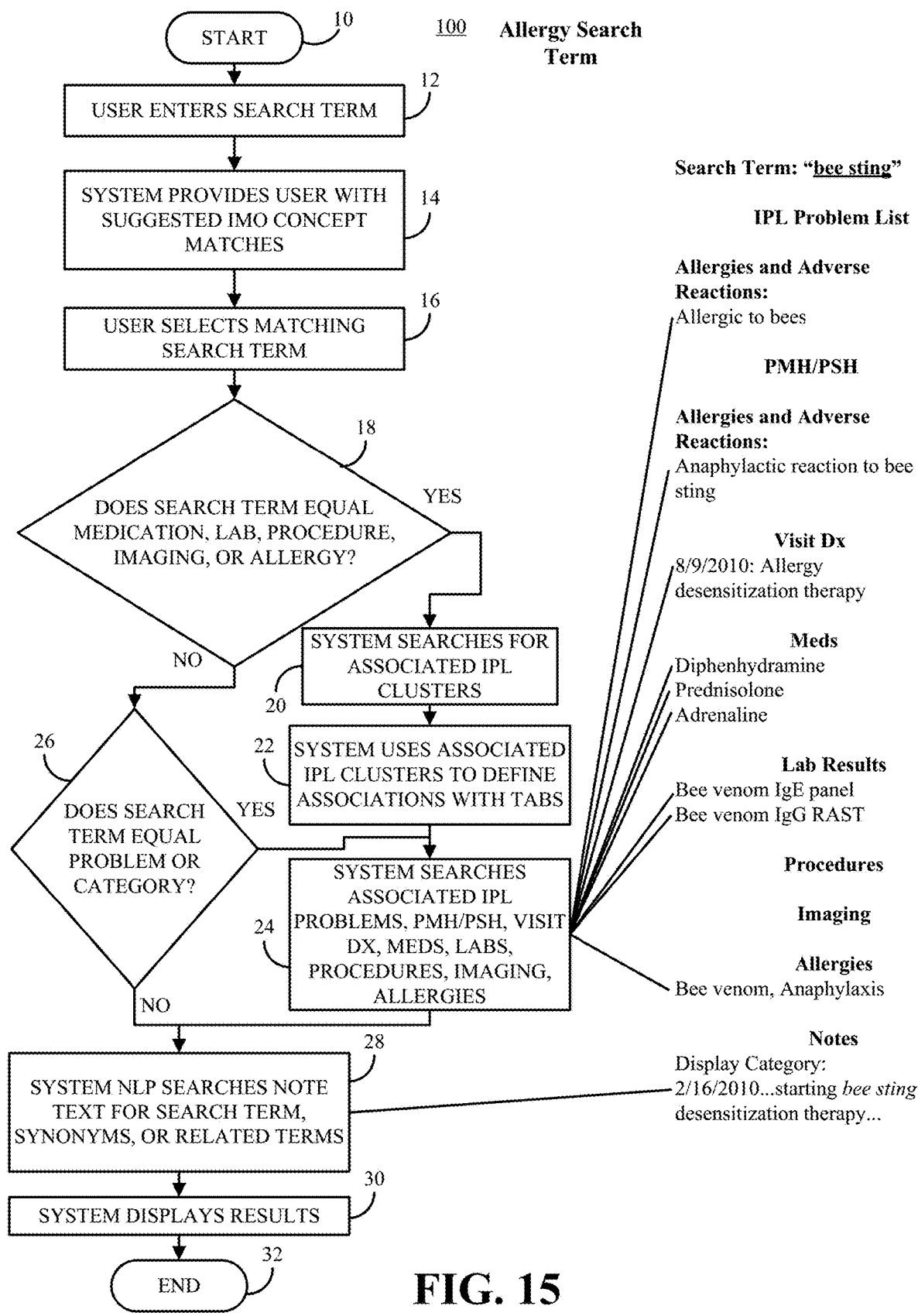
FIG. 15 is an example of the flowchart and analytical methodology of FIG. 8 when the search term corresponds to allergy-related information.

FIG. 15 depicts a seventh example of this methodology, but where the search term, or the user's selection of a match to the search term, represents an allergy. For example, the user's search term "bee sting" may result in the user selecting a matching term "bee sting" or "bee venom, anaphylaxis."

Figure 17:
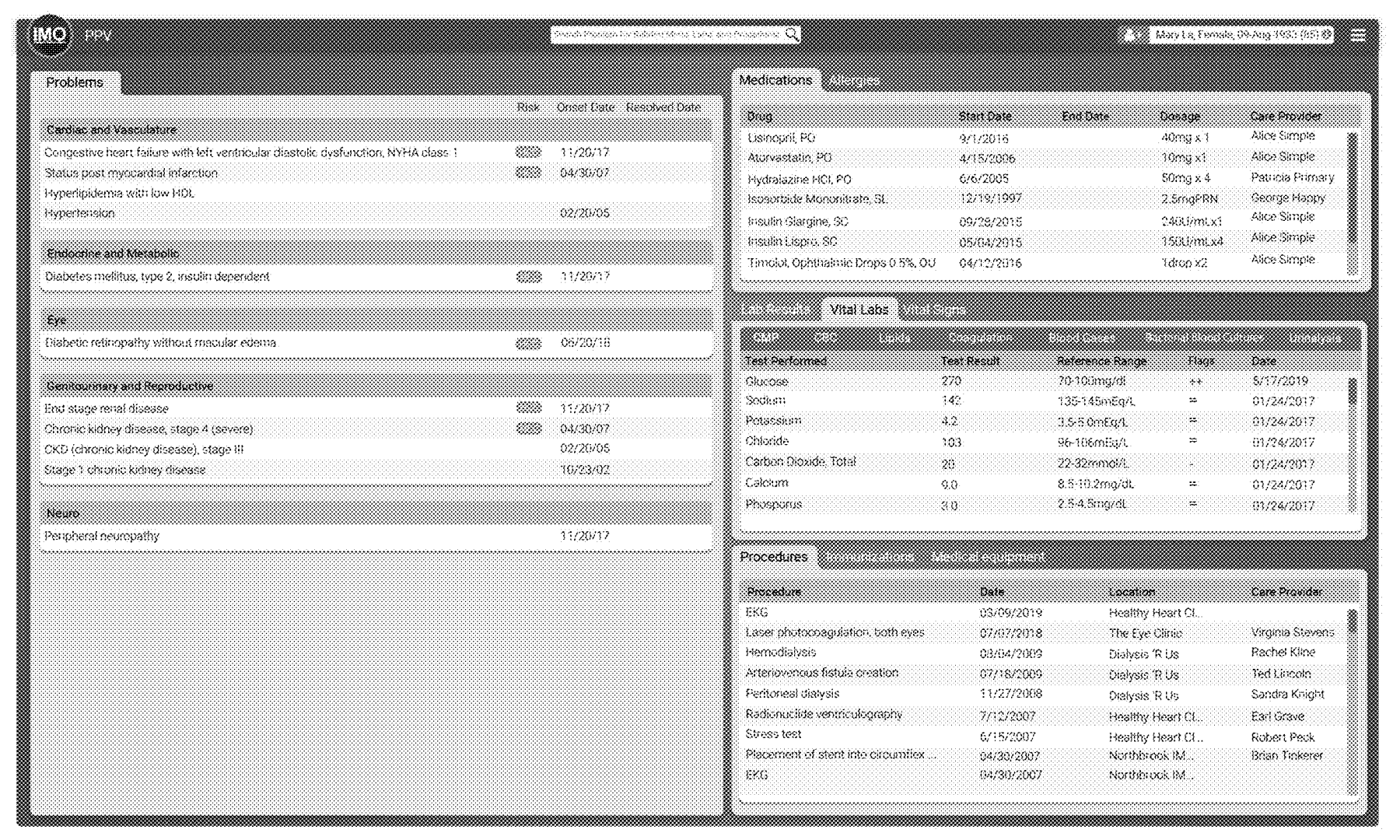

FIGS. 16-21 present various images of a graphical user interface for carrying out the method steps described above. In particular, FIG. 16 depicts a user interface after a specific patient is selected, the interface including a first region identifying and orienting problem list elements in a plurality of categories according to the methodology previously discussed herein. The user interface also includes one or more second regions identifying and orienting the other types of patient health record data discussed above. In this particular example, the regions may include tabs or other selectors permitting the user to toggle between different types of data. For example, a medications tab permits a region with medication-related data to be brought to the forefront of the interface, and an allergies tab permits a user to access a region with allergies-related data. By selecting the allergies tab, that data may be brought to a foreground, thereby relegating the medications data to an inactive part of the interface. FIG. 17 depicts a similar interface but one on which the "Vital Labs" section has been selected, thereby bringing it to the forefront of its region of the user interface while sending the "Lab Results" section rearward (or otherwise hiding that section, other than its tab).

Figure 18:
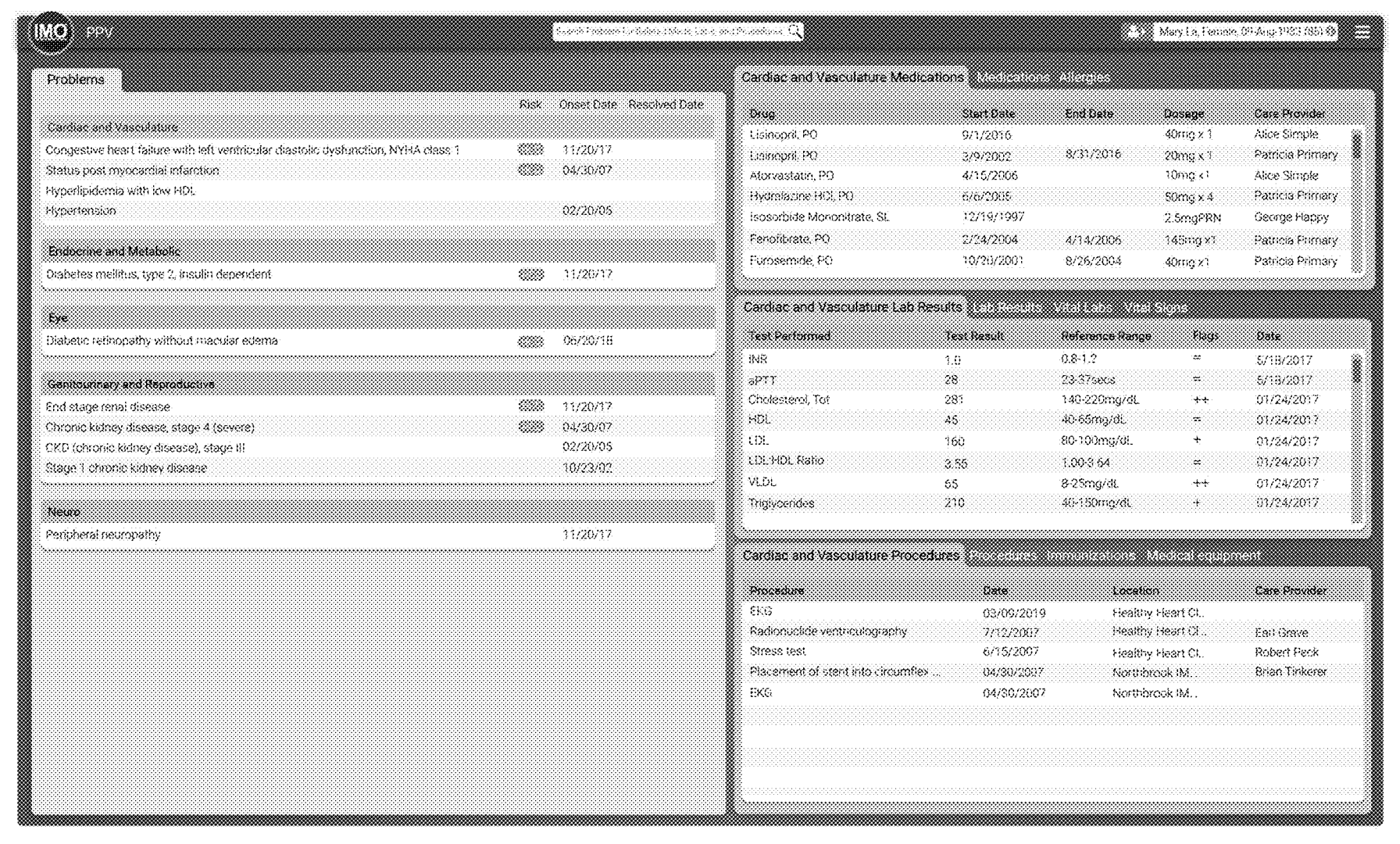

Turning to FIG. 18, an aspect of the user interface is depicted in which the user has selected one of the problem list categories, e.g., by selecting it header in the ordered problem list section of the interface. This functionality is similar to the methodology described and shown with respect to FIG. 10, where the user input or search term is received via a user selection within a portion of the interface. It will be appreciated that other methods of receiving a user input or search term are possible, such as through receiving input in the search bar at the top of the interface via an input/out device such as a keyboard or touch pad. In this example, the system receives a user selection of the "Cardiac and Vasculature" category. Using the methodology described above, the system then may display all Cardiac and Vasculature-related medications, lab results, and procedures (both current and historical) by generic type. As can be seen in FIG. 18, the system may generate concept- or cluster-specific tabs in addition to generic ones. For example, in addition to a tab presenting the user with Cardiac and Vasculature-related medications, the user interface also may include a tab to medications, generally. As such, a user may be able to quickly view the specific medications, labs, etc., that are relevant to the user's search while also quickly and easily permitting the user to view all medications, labs, etc., relevant to the patient.

Figure 19:
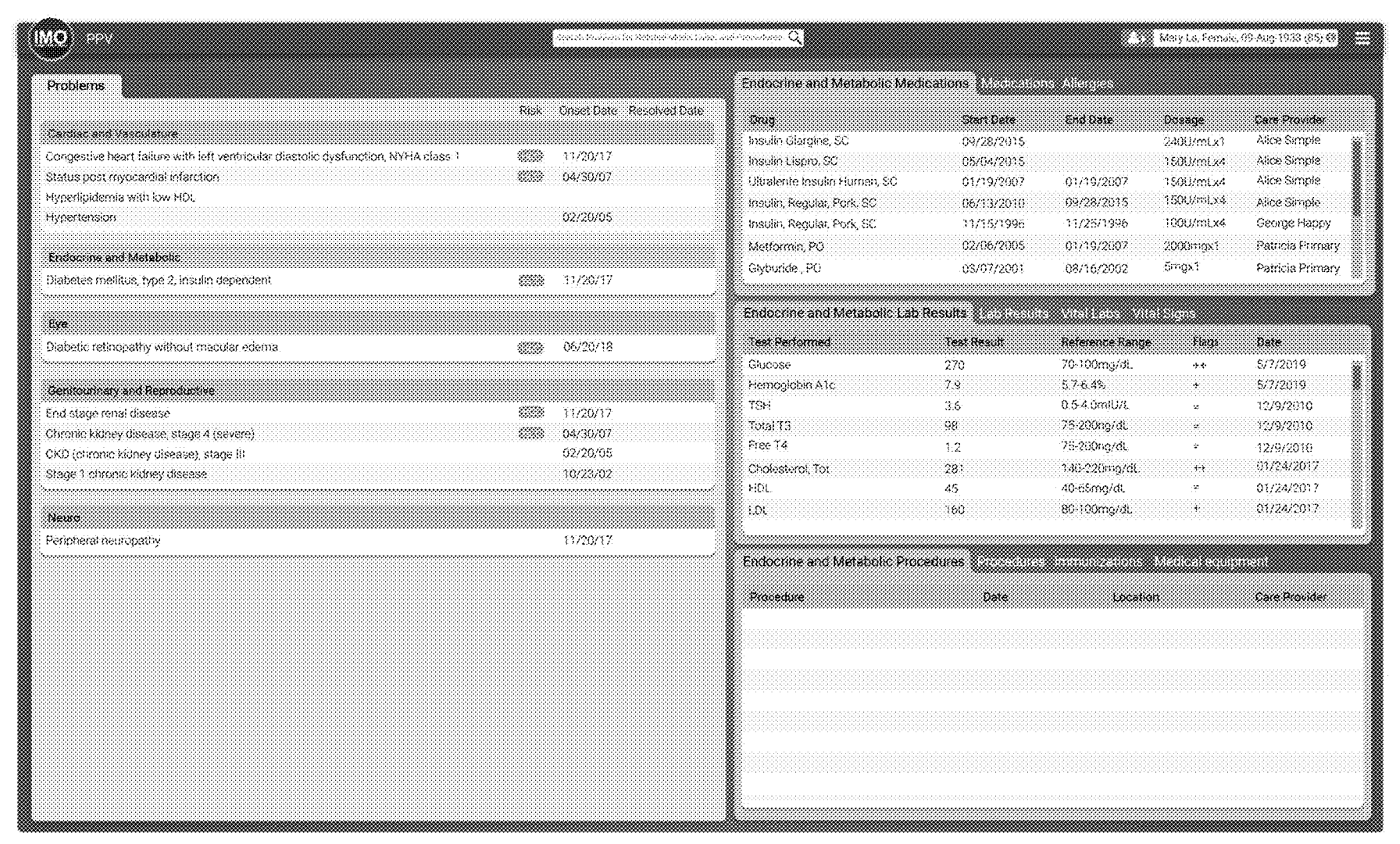
Figure 20:
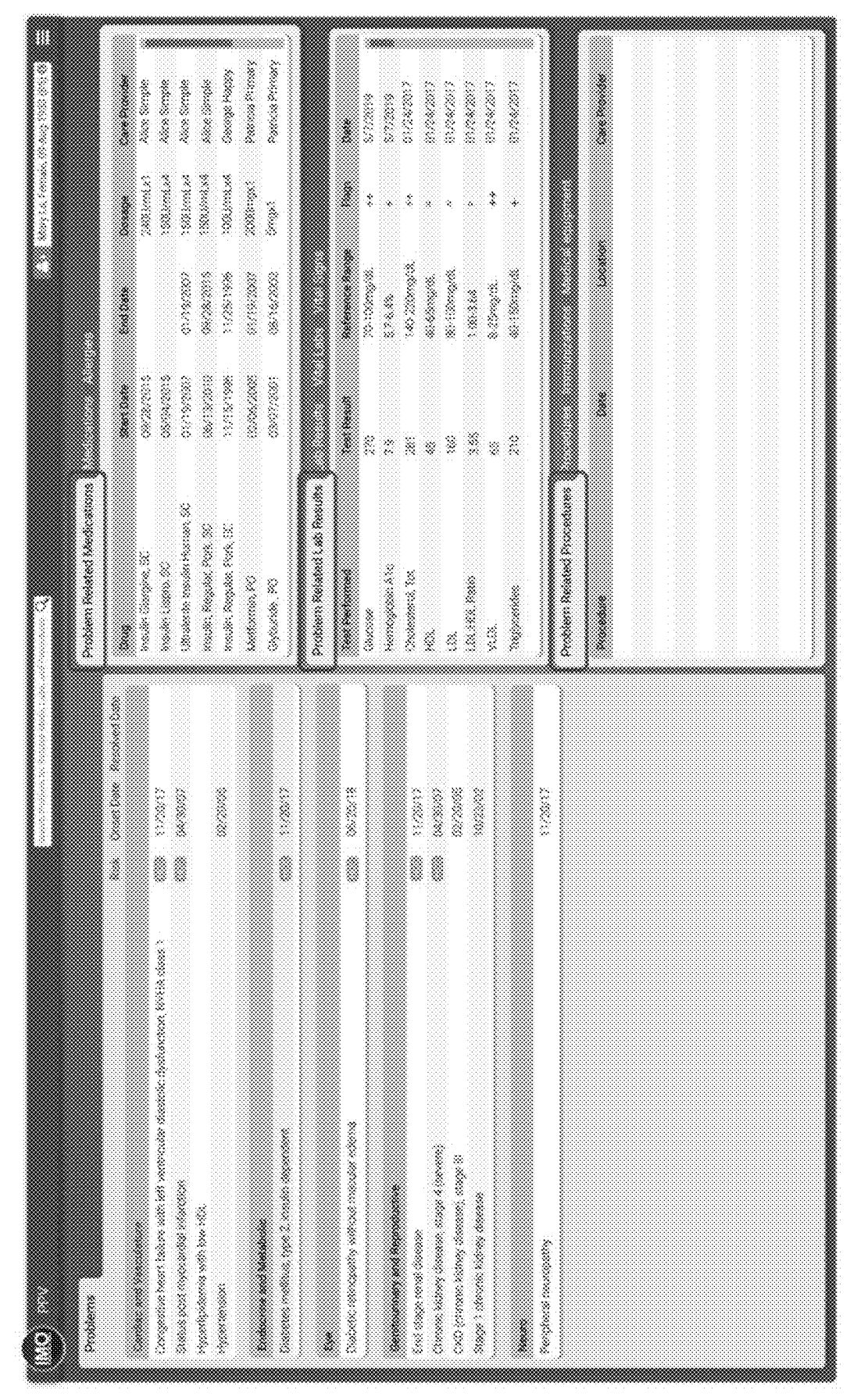

FIGS. 19 and 20 depict aspects of the user interface highlighting a distinction between a user selection of a category of problems and a user selection of a specific problem. In particular, FIG. 19 (like FIG. 18) illustrates an example of a user selecting an "Endocrine and Metabolic" category of problems. Based on that selection, and using the methodology described above, the system may generate Endocrine and Metabolic specific portions of the user interface directed to medications, lab results, and procedures. (In this instance, the specific patient does not have any Endocrine and Metabolic-related procedures in her record, so that that portion of the interface appears empty.) It will be appreciated that, even though the patient's problem list only includes a diabetes-related problem within this category, i.e., "Diabetes Mellitus, type 2, insulin dependent," the system has identified lab results in the patient's record that relate to both diabetes and thyroid-related (endocrine) problems.

In contrast, FIG. 20 illustrates an example of the user specifically selecting the "Diabetes Mellitus, type 2, insulin dependent" problem within the Endocrine and Metabolic category. By selecting a specific problem, the user interface may be modified to provide medications, lab results, and procedures specifically mapped to that problem. For example, as compared to the interface of FIG. 19, the diabetes-related medications, lab results, and procedures also are displayed in the interface of FIG. 20, but the thyroid-related ones are omitted. (Due to the length of the selected problem, the user interface may modify its problem-specific headers to include an abbreviation of the problem or other manner of indicating that the medications, lab results, procedures, etc., relate to the selected problem.)

Figure 21:
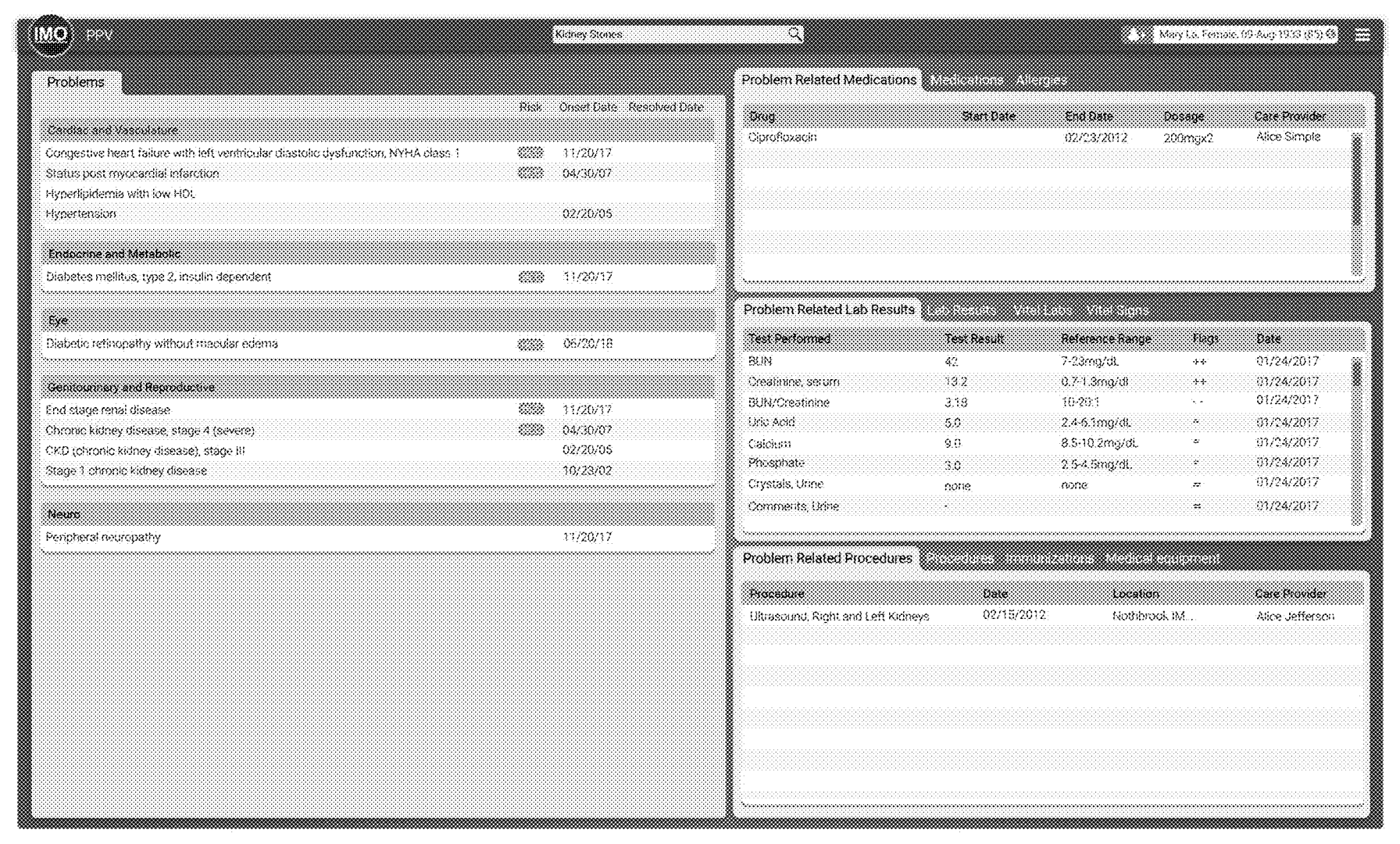

FIG. 21 provides a depiction of a user interface for carrying out the method in which the term searched by the user corresponds to a problem, but one that is not on the patient's problem list. In this example, the user searches for "kidney stones," but it can be seen no "kidney stone" problem or "kidney stone"-related problem exists on the problem list on the left-hand side of the user interface. However, the system recognizes that "kidney stone" relates to a valid problem, that that problem exists in one or more clusters within the categories of possible problems, and that various medications, labs, and procedures that are contained in the patient's electronic health record are mapped to either the kidney stone problem or to one or more other problems with which that problem is clustered. The system then generates problem-specific windows within the user interface to present those medications, labs, and procedures. In this manner, the system also may function as a differential diagnosis tool, permitting the user to analyze the patient's electronic health record data to determine whether it includes sufficient information to potentially include or affirmatively exclude a problem from the patient's problem list not already on that list. In one aspect, should the information presented to the user be sufficient for the user to conclude that the patient likely has or at some point had the additional problem, the user interface may be configured to permit the It should be appreciated that, although the examples provided above only present the user with specific medications, labs, and procedures, similar analysis can be performed for imaging and allergy results, as well, with similar problem- or category-specific regions generated in the user interface to present those imaging and allergy results.

As discussed above, the system may receive a user input and associate a specific profile with that input, so that upon logging in, the interface presented to the user is tailored to that user's specific needs or preferences. For example, the problems most relevant to a cardiologist may be different than those most relevant to an orthopedic surgeon. In a similar fashion, the system may be configured to provide specialty views by generating specific clusters tailored to those specialties. For example, an "anesthesiology" cluster may incorporate specific pulmonary, cardiology, and allergy-related data. Similarly, a "transplant medicine" cluster may incorporate specific hematology, oncology, and immunology-related data. One notable point is that, unlike the other clusters described above, these specialty clusters may not be considered subsets of any of the categories described above.

The systems described above may be implemented in one or more ways in order to make it accessible to the user. In one instance, the system may be accessible as a software as a service (SaaS) application. Alternatively, the system may be linked to or integrated into a vendor's software application accessible through an application program interface (API). In addition, the present system and method may employ data classes supported by the US Core Data for Interoperability (USCDI). As a result, the system also may be configured to support the Consolidated-Clinical Document Architecture (C-CDA) standard provided by Health Level 7 (HL7) and/or the SMART on FHIR interoperability protocols. The HL7 Consolidated CDA is an implementation guide that specifies a library of templates using the clinical data architecture (CDA) schema and prescribes their use for a set of specific document types. Similarly, SMART provides a standard for how EHR systems and their applications authenticate and integrate. FHIR provides an API and a set of data models for structuring and accessing medical data. SMART on FHIR refers to a SMART-compliant EHR system on top of a FHIR server.

By having data structured and/or data classes selected so as to comply with these standards, the system also may be configured to operate in multiple different electronic health record environments, including a standalone, single EHR system, across a network of providers, or in connection with a health information exchange (HIE).

While the foregoing written description enables one of ordinary skill to make and use the same, those of ordinary skill also will understand and appreciate the existence of variations, combinations, and equivalents of the specific exemplary embodiments and methods disclosed herein. The claims should therefore not be limited by the above described embodiment and method but should be interpreted within the scope and spirit of the invention as claimed.

What is claimed is:

1. A method for identifying patient-specific care plans through a patient-specific problem list in an electronic medical record or an electronic health record, comprising:
    mapping, using a computer, entries in a problem list with a respective description in an interface terminology, wherein the interface terminology comprises a plurality of domains, a plurality of concepts, and a plurality of descriptions, wherein each concept is unique within a given domain, and wherein each description maps to a respective concept in the interface terminology and is an alternative way to express the respective concept;
    analyzing, by a computer, interface terminology concepts mapped to each mapped entry to determine related problem list entries;
    grouping related entries into one or more problem list categories;
    for each problem in a problem list category, identifying one or more care plans triggered by the problem;
    for each problem list category, aggregating the one or more care plans triggered by each problem in that category into one or more types of care plans;
    accessing a user profile stored on a computer; and
    displaying each type of care plan in separate regions of the graphical user interface, each region including a unique header wherein the regions are dynamically arranged in the user interface in accordance with the user profile.

2. The method of claim 1, wherein the patient-specific problem list triggering the one or more care plans includes both previous and current medical conditions.

3. The method of claim 2, wherein the one or more care plans triggered by the previous and current medial conditions include previous and current care plans.

4. The method of claim 1, wherein the types of care plans include one or more of medications, laboratory tests, or procedures.

* * * * *